(12) United States Patent
Ramezani et al.

(10) Patent No.: US 10,937,547 B2
(45) Date of Patent: Mar. 2, 2021

(54) SUBJECT ASSESSMENT USING LOCALIZATION, ACTIVITY RECOGNITION AND A SMART QUESTIONNAIRE

(71) Applicants: THE REGENTS OF THE UNIVERSITY OF CALIFORNIA, Oakland, CA (US); Ramin Ramezani, Los Angeles, CA (US); Babak Moatamed, Los Angeles, CA (US); Arjun, Los Angeles, CA (US); Arash Naeim, Los Angeles, CA (US); Majid Sarrafzadeh, Anaheim Hills, CA (US)

(72) Inventors: Ramin Ramezani, Los Angeles, CA (US); Babak Moatamed, Los Angeles, CA (US); Arjun, Los Angeles, CA (US); Arash Naeim, Los Angeles, CA (US); Majid Sarrafzadeh, Anaheim Hills, CA (US)

(73) Assignee: The Regents of the University of California, Oakland, CA (US)

( * ) Notice: Subject to any disclaimer, the term of this patent is extended or adjusted under 35 U.S.C. 154(b) by 479 days.

(21) Appl. No.: 15/736,744

(22) PCT Filed: Jun. 14, 2016

(86) PCT No.: PCT/US2016/037398
§ 371 (c)(1),
(2) Date: Dec. 14, 2017

(87) PCT Pub. No.: WO2016/205212
PCT Pub. Date: Dec. 22, 2016

(65) Prior Publication Data
US 2018/0190382 A1 Jul. 5, 2018

Related U.S. Application Data

(60) Provisional application No. 62/175,840, filed on Jun. 15, 2015, provisional application No. 62/330,730, filed on May 2, 2016.

(51) Int. Cl.
*H04W 4/20* (2018.01)
*G16H 50/20* (2018.01)
(Continued)

(52) U.S. Cl.
CPC ............ *G16H 50/20* (2018.01); *A61B 5/1118* (2013.01); *A61B 5/7267* (2013.01); *G06F 1/16* (2013.01);
(Continued)

(58) Field of Classification Search
CPC ..... H04L 67/12; H04L 63/1412; H04L 41/22; H04L 67/1097; H04W 4/70; H04W 4/20; H04W 4/021; H04W 4/02
See application file for complete search history.

(56) References Cited

U.S. PATENT DOCUMENTS 10,069,781 B2 * 9/2018 Kumar .................... H04L 51/18
10,313,289 B2 * 6/2019 Kumar .................... H04W 4/70
(Continued)

FOREIGN PATENT DOCUMENTS

WO         2010108287 A1    9/2010
WO    WO-2010/108287 A1    9/2010
(Continued)

OTHER PUBLICATIONS

Hillestad et al., "Can Electronic Medical Record Systems Transform Health Care? Potential Health Benefits, Savings, and Costs", Health Affairs, vol. 24, No. 5, Sep.-Oct. 2005, pp. 1103-1117.
(Continued)

*Primary Examiner* — William D Cumming
(74) *Attorney, Agent, or Firm* — KPPB LLP

(57) ABSTRACT

A method for subject assessment in an environment includes receiving subject sensor data from a sensor positioned adjacent to a subject, receiving beacon signals from a beacons placed at different positions within the environ-
(Continued)

ment, processing the beacon signals to determine a location of the subject within the environment based on relative power levels of the received beacon signals, and processing the subject sensor data to determine an activity of the subject.

19 Claims, 6 Drawing Sheets

(51) Int. Cl.

| | |
|---|---|
| G06N 20/00 | (2019.01) |
| H04L 29/10 | (2006.01) |
| H04L 29/08 | (2006.01) |
| G06F 1/16 | (2006.01) |
| A61B 5/11 | (2006.01) |
| A61B 5/00 | (2006.01) |
| G16H 20/30 | (2018.01) |
| G16H 40/63 | (2018.01) |
| G06N 5/00 | (2006.01) |
| G16H 10/20 | (2018.01) |
| G06N 5/04 | (2006.01) |
| G06N 7/00 | (2006.01) |
| G06F 3/0482 | (2013.01) |

(52) U.S. Cl.
CPC ............. *G06F 1/163* (2013.01); *G06N 5/003* (2013.01); *G06N 5/045* (2013.01); *G06N 5/047* (2013.01); *G06N 7/005* (2013.01); *G06N 20/00* (2019.01); *G16H 10/20* (2018.01); *G16H 20/30* (2018.01); *G16H 40/63* (2018.01); *H04L 29/08* (2013.01); *H04L 29/10* (2013.01); *H04L 67/04* (2013.01); *H04L 67/12* (2013.01); *H04L 67/22* (2013.01); *A61B 5/002* (2013.01); *A61B 5/0022* (2013.01); *A61B 5/1116* (2013.01); *A61B 5/681* (2013.01); *A61B 5/6898* (2013.01); *A61B 2560/0209* (2013.01); *G06F 3/0482* (2013.01)

(56) References Cited

U.S. PATENT DOCUMENTS

| | | | | |
|---|---|---|---|---|
| 10,499,228 | B2* | 12/2019 | Padgett | G07C 9/00309 |
| 2007/0133352 | A1 | 6/2007 | Kim et al. | |
| 2007/0135866 | A1 | 6/2007 | Baker et al. | |
| 2008/0139899 | A1 | 6/2008 | Student et al. | |
| 2015/0078140 | A1 | 3/2015 | Riobo Aboy et al. | |
| 2017/0093952 | A1* | 3/2017 | Kumar | H04L 67/22 |
| 2018/0190382 | A1* | 7/2018 | Ramezani | H04L 67/22 |
| 2018/0375810 | A1* | 12/2018 | Kumar | H04L 67/22 |
| 2019/0007354 | A1* | 1/2019 | Bulut | G16H 40/63 |
| 2019/0159003 | A1* | 5/2019 | Padgett | G07C 9/28 |
| 2019/0207894 | A1* | 7/2019 | Kumar | H04L 67/22 |
| 2020/0004583 | A1* | 1/2020 | Kelly | G06N 20/00 |
| 2020/0014708 | A1* | 1/2020 | Cohen | G06N 7/005 |
| 2020/0042928 | A1* | 2/2020 | Kim | G06Q 10/06398 |
| 2020/0059774 | A1* | 2/2020 | Padgett | G07C 9/27 |
| 2020/0103894 | A1* | 4/2020 | Cella | G06N 3/088 |
| 2020/0117900 | A1* | 4/2020 | Deng | H04W 4/02 |
| 2020/0120170 | A1* | 4/2020 | Amitay | H04W 4/021 |
| 2020/0133254 | A1* | 4/2020 | Cella | G06N 3/0472 |
| 2020/0133255 | A1* | 4/2020 | Cella | G05B 19/41865 |
| 2020/0133256 | A1* | 4/2020 | Cella | G05B 23/0286 |
| 2020/0133257 | A1* | 4/2020 | Cella | G05B 23/024 |
| 2020/0150643 | A1* | 5/2020 | Cella | G05B 23/0289 |
| 2020/0150644 | A1* | 5/2020 | Cella | G06N 3/0454 |
| 2020/0150645 | A1* | 5/2020 | Cella | G05B 23/0297 |

FOREIGN PATENT DOCUMENTS

| | | |
|---|---|---|
| WO | 2011042829 A1 | 4/2011 |
| WO | 2012038783 A1 | 3/2012 |
| WO | 2016205212 A1 | 12/2016 |

OTHER PUBLICATIONS

Holden et al., "The technology acceptance model: its past and its future in health care", Journal of Biomedical Informatics, vol. 43, No. 1, Feb. 2010, Electronic Publication: Jul. 15, 2009, 30 pgs.
Humphrey et al., "Super-Resolution Time of Arrival for Indoor Localization", IEEE International Conference on Communications, May 19-23, 2008, 5 pgs.
Hurria et al., "Developing a Cancer-Specific Geriatric Assessment: A Feasibility Study", American Cancer Society, vol. 104, No. 9, Nov. 1, 2005, pp. 1998-2005.
Jang et al., "Simple Prognostic Model for Patients with Advanced Cancer Based on Performance Status", Journal of Oncology Practice, vol. 10, No. 5, Sep. 2014, Electronic Publication: Aug. 12, 2014, pp. 335-341.
Jefferis et al., "Trajectories of Objectively Measured Physical Activity in Free-Living Older Men", Medicine and Science in Sports and Exercise, vol. 47, No. 2, Feb. 2015, pp. 343-349.
Kaiser et al., "Validation of the Mini Nutritional Assessment short-form (MNA-SF): a practical tool for identification of nutritional status", Journal of Nutrition, Health, and Aging, vol. 13, No. 9, Nov. 2009, pp. 782-788.
Kang et al., "Improved Heading Estimation for Smartphone-Based Indoor Positioning Systems", IEEE International Symposium on Personal, Indoor, and Mobile Radio Communications, Sep. 9-12, 2012, 5pgs.
Kenis et al., "Relevance of a systematic geriatric screening and assessment in older patients with cancer: results of a prospective multicentric study", Annals of Oncology, vol. 24, No. 5, May 2013, Published Online: Jan. 4, 2013, pp. 1306-1312.
Kroenke et al., "Operating Characteristics of PROMIS Four-Item Depression and Anxiety Scales in Primary Care Patients with Chronic Pain", Pain Medicine, vol. 15, No. 11, Nov. 2014, Electronic Publication: Aug. 19, 2014, pp. 1892-1901.
Kwapisz et al., "Activity Recognition using Cell Phone Accelerometers", ACM SIGKDD Explorations Newsletter, vol. 12, No. 2, Dec. 2010, pp. 74-82.
Lan et al., "SmartFall: An Automatic Fall Detection System Based on Subsequence Matching for the SmartCane", BodyNets International Conference on Body Area Networks, Apr. 1-3, 2009, 8 pgs.
Lan et al., "WANDA: An End-to-End Remote Health Monitoring and Analytics System for Heart Failure Patients", Conference on Wireless Health, ACM, Oct. 23-25, 2012, 8 pgs.
Lara et al., "A Survey on Human Activity Recognition using Wearable Sensors", IEEE Communications Surveys & Tutorials, vol. 15, No. 3, Third Quarter 2013, pp. 1192-1209.
Lee et al., "Remote Patient Monitoring: What Impact Can Data Analytics Have on Cost?", Conference on Wireless Health, Nov. 1-3, 2013, 8 pgs.
Li et al., "A Reliable and Accurate Indoor Localization Method Using Phone Inertial Sensors", Proceedings of the ACM Conference on Ubiquitous Computing, Sep. 5-8, 2012, pp. 421-430.
Li et al., "Indoor Positioning Techniques Based on Wireless LAN", IEEE International Conference on Wireless Broadband and Ultra Wideband Communications, Sep. 24-27, 2006, 7 pgs.
Li et al., "Super-Resolution TOA Estimation With Diversity for Indoor Geolocation", IEEE Transactions on Wireless Communications, vol. 3, No. 1, Jan. 14, 2004, pp. 224-234.
Lin et al., "Screening for cognitive impairment in older adults: A systematic review for the U.S. Preventive Services Task Force", Annals of Internal Medicine, vol. 159, No. 9, Nov. 5, 2013, pp. 601-612.
Liu et al., "Survey of wireless indoor positioning techniques and systems", Systems, Man and Cybernetics, Part C: Applications and Reviews, IEEE Transaction on, vol. 37, No. 6, pp. 1067-1080.

(56) References Cited

OTHER PUBLICATIONS

Lu et al., "Robust Location-Aware Activity Recognition Using Wireless Sensor Network in an Attentive Home", IEEE Transactions on Automation Science and Engineering, vol. 6, No. 4, pp. 598-609.
Luciani et al., "Detecting Disabilities in Older Patients With Cancer: Comparison Between Comprehensive Geriatric Assessment and Vulnerable Elders Survey-13", Journal of Clinical Oncology, vol. 28, No. 12, Apr. 20, 2010, Electronic Publication: Mar. 22, 2010, pp. 2046-2050.
Mariotto et al., "Projections of the Cost of Cancer Care in the United States: 2010-2020", Journal of the National Cancer Institute, vol. 103, No. 2, Jan. 19, 2011, Advance Publication: Jan. 12, 2011, pp. 117-128.
Martin et al., "Enhancing Context Awareness with Activity Recognition and Radio Fingerprinting", Proceedings of the 5th IEEE International Conference on Semantic Computing, Palo Alto, CA, Sep. 18-21, 2011, 4 pgs.
Mautz, "Indoor Positioning Technoloogies", Habilitation Thesis, EHT Zurich, Switzerland, 2012, 129 pgs.
McCleary et al., "Feasibility of Computer-Based Self-Administered Cancer-Specific Geriatric Assessment in Older Patients With Gastrointestinal Malignancy", The Oncologist, vol. 18, No. 1, Jan. 3, 2013, pp. 64-72.
Meguerdichian et al., "Exposure in Wireless Ad-Hoc Sensor Networks", Proceedings of the International Conference on Mobile Computing and Networking, Jul. 16-21, 2001, pp. 139-150.
Michie et al., "The behaviour change wheel: a new method for characterising and designing behaviour change interventions", Implementation Science, vol. 6, No. 1, 42, published online Apr. 23, 2011, 11 pgs.
Mortazavi et al., "Determining the Single Best Axis for Exercise Repetition Recognition and Counting with SmartWatches", IEEE International Conference on Wearable and Implantable Body Sensor Networks, Jun. 16-19, 2014, 6 pgs.
Mortellaro et al., "Performance characterization of an abiotic and fluorescent-based continuous glucose monitoring system in patients with type 1 diabetes", Biosensors and Bioelectronics, vol. 61, Nov. 15, 2014, Available Online: May 17, 2014, pp. 227-231.
Najafi et al., "Novel Wearable Technology for Assessing Spontaneous Daily Physical Activity and Risk of Falling in Older Adults with Diabetes", Journal of Diabetes Science and Technology, vol. 7, No. 5, Sep. 1, 2013, pp. 1147-1160.
Ni et al., "LANDMARC: Indoor Location Sensing Using Active RFID", Wireless Networks, vol. 10, 2004, pp. 701-710.
Niculescu et al., "Ad hoc positioning system (APA) using AOA", IEEE INFOCOM 2003, Mar. 30-Apr. 3, 2003, 10pgs.
Noury et al., "Fall detection—Principles and Methods", IEEE International Conference of Engineering in Medicine and Biology, Aug. 23-26, 2007, pp. 1663-1666.
Ortman et al., "An aging nation: the older population in the United States", U.S. Census Bureau, 25-1140, 28 pgs.
Paap et al., "Identifying key domains of health-related quality of life for patients with Chronic Obstructive Pulmonary Disease: the patient perspective", Health and Quality of Life Outcomes, vol. 12, No. 1, 2014, 13 pgs.
Pahlavan et al., "Indoor geolocation science and technology", IEEE Communications Magazine, vol. 40, No. 2, Feb. 2002, pp. 112-118.
Pahlavan et al., "Wideband Radio Propagation Modeling for Indoor Geolocation Applications", IEEE Communications Magazine, vol. 36, No. 4, Apr. 1998, pp. 60-65.
Park et al., "A Watch-type Human Activity Detector for the Aged Care", IEEE International Conference on Advanced Communication Technology, Feb. 19-22, 2013, pp. 648-652.
Paul et al., "RSSI-Based Indoor Localization and Tracking Using Sigma-Point Kalman Smoothers", IEEE Journal of Selected Topics in Signal Processing, vol. 3, No. 5, Oct. 2009, pp. 860-873.
Pourhomayoun et al., "A novel method for medical implant in-body localization", IEEE International Conference of Engineering in Medicine and Biology, Aug. 28-Sep. 1, 2012, 5 pgs.
Pourhomayoun et al., "Indoor Localization, Tracking and Fall Detection for Assistive Healthcare Based on Spatial Sparsity and Wireless Sensor Network", International Journal of Monitoring and Surveillance Technologies Research, vol. 1, No. 2, Apr. 2013, 6 pgs.
Pourhomayoun et al., "Spatial Sparsity Based Emitter Localization", Conference on Information Sciences and Systems, Mar. 21-23, 2012, 4 pgs.
International Written Opinion and Search Report for International Application No. PCT/US2016/037398, dated Sep. 19, 2016.
Pourhomayoun et al., "Spatial sparsity based indoor localization in wireless sensor network for assistive healthcare", IEEE International Conference of the Engineering in Medicine and Biology, Aug. 28-Sep. 1, 2012, pp. 3696-3699.
Prichep et al., "Classification of Traumatic Brain Injury Severity Using Informed Data Reduction in a Series of Binary Classifier Algorithms", IEEE Transactions on Neural Systems and Rehabilitation Engineering, vol. 20, No. 6, Nov. 2012, pp. 806-822.
Priyantha et al., "The Cricket Location-Support System", Proceedings of the International Conference on Mobile Computing and Networking, Aug. 6-11, 2000, pp. 32-43.
Ravi et al., "Activity Recognition from Accelerometer Data", American Association for Artificial Intelligence, 2005, pp. 1541-1546.
Riboni et al., "COSAR: Hybrid Reasoning for Context-aware Activity Recognition", Personal and Ubiquitous Computing, vol. 15, No. 3, Mar. 2011, pp. 271-289.
Savvides, Andreas et al. , "Dynamic Fine-Grained Localization in Ad-Hoc Networks of Sensors", In Mobile Computing and Networking, pp. 166-179, 2001.
Saxena et al., "Experimental Analysis of Rssi-Based Outdoor Localization in Wireless Sensor Networks", International Conference on Communication Systems Software and Middleware and Workshops, Jan. 6-10, 2008, pp. 503-510.
Sheikh, "Accurate WiFi-Based Localization of Dementia Patients for Caregiver Support", Grantome, National Institutes of Health, printed from the World Wide Web on Jan. 28, 2016, 3 pgs.
Sokal et al., "Network of Movement and Proximity Sensors for Monitoring Upper-Extremity Motor Activity After Stroke: Proof of Principle", Archives of Physical Medicine and Rehabilitation, vol. 95, No. 3, Mar. 2014, Published Online: Sep. 30, 2013, pp. 499-505.
Soubeyran et al., "Predictors of Early Death Risk in Older Patients Treated With First-Line Chemotherapy for Cancer", Journal of Clinical Oncology, vol. 30, No. 15, May 20, 2012, Electronic Publication: Apr. 16, 2012, pp. 1829-1834.
Stepnowsky Jr et al,, "Pilot Randomized Trial of the Effect of Wireless Telemonitoring on Compliance and Treatment Efficacy in Obstructive Sleep Apnea", Journal of Medical Internet Research, vol. 9, No. 2, Apr.-Jun. 2007, Published Online: May 17, 2007, pp. 1-22.
Stucki et al., "A Web-Based Non-Intrusive Ambient System to Measure and Classify Activities of Daily Living", Journal of Medical Internet Research, vol. 16, No. 7, Jul. 21, 2014, 12pgs.
Stukenborg et al., "Cancer patient-reported outcomes assessment using wireless touch screen tablet computers", Quality of Life Research, vol. 23, No. 5, Jun. 2014, Electronic Publication: Dec. 4, 2013, pp. 1603-1607.
Subhan et al., "Indoor Positioning in Bluetooth Networks using Fingerprinting and Lateration approach", IEEE International Conference on Information Science and Applications, Apr. 26-29, 2011, pp. 1-9.
Suh et al., "A Remote Patient Monitoring System for Congestive Heart Failure", Journal of Medical Systems, vol. 35, No. 5, Oct. 2011, Electronic Publication: May 25, 2011, pp. 1165-1179.
Suh et al., "An Automated Vital Sign Monitoring System for Congestive Heart Failure Patients", ACM International Health Informatics Symposium, Nov. 11-12, 2010, pp. 108-117.
Suh et al., "Dynamic Self-adaptive Remote Health Monitoring System for Diabetics", IEEE International Conference on Engineering in Medicine and Biology, 2012, pp. 2223-2226.
Suh et al., "Missing Data Imputation for Remote CHF Patient Monitoring Systems", IEEE International Conference on Engineering in Medicine and Biology, 2011, pp. 3184-3187.

(56) References Cited

OTHER PUBLICATIONS

Suh et al., "WANDA B.: Weight and Activity with Blood Pressure Monitoring System for Heart Failure Patients", IEEE Transactions on Information Technology in Biomedicine, Jun. 14, 2010, pp. 1-6.
Swersky et al., "Multi-task Bayesian Optimization", Proceedings of International Conference on Neural Information Processing Systems, vol. 2, Dec. 5-10, 2013, pp. 2004-2012.
Thielke et al., "Associations Between Observed In-Home Behaviors and Self-Reported Low Mood in Community-Dwelling Older Adults", Journal of the American Geriatrics Society, vol. 62, No. 4, Apr. 2014, Published Online: Mar. 17, 2014, pp. 685-689.
Ustun et al., "Facilitating the application of Support Vector Regression by using a universal Pearson VII function based kernel", Chemometrics and Intelligent Laboratory Systems, vol. 81, No. 1, Mar. 2006, pp. 29-40.
Uswatte et al., "Ambulatory Monitoring of Arm Movement Using Accelerometry: An Objective Measure of Upper-Extremity Rehabilitation in Persons With Chronic Stroke", Archives of Physical Medicine and Rehabilitation, vol. 86, No. 7, Jul. 2005, pp. 1498-1501.
Vaha-Ypya et al., "A universal, accurate intensity-based classification of different physical activities using raw data of accelerometer", Clinical Physiology and Functional Imaging, vol. 35, No. 1, Jan. 2015, Electronic Publication: Jan. 7, 2014, pp. 64-70.
Villalba et al., "Wearable and Mobile System to Manage Remotely Heart Failure", IEEE Transactions on Information Technology in Biomedicine, vol. 13, No. 6, Nov. 2009, Date of Publication: Jul. 28, 2009, pp. 990-996.
Wiens et al., "Learning Evolving Patient Risk Processes for C. Diff Colonization", ICML Workshop on Clinical Data Analysis, 2012, 8 pgs.
Wildiers et al., "International Society of Geriatric Oncology Consensus on Geriatric Assessment in Older Patients with Cancer", Journal of Clinical Oncology, vol. 32, No. 24, Aug. 20, 2014, pp. 2595-2603.
Wyffels et al., "A Novel Indoor Localization System for Healthcare Environments", IEEE International Symposium on Computer-Based Medical Systems, Jun. 20-22, 2012, 6 pgs.
Wyffels et al., "Distributed, Signal Strength based Indoor Localization Algorithm for Use in Healthcare Environments", IEEE Journal of Biomedical and Health Informatics, vol. 18, No. 6, Nov. 2014, Date of Publication: Jan. 27, 2014, pp. 1887-1893.
Wyffels et al., "Using a Decision Tree for Real-Time Distributed Indoor Localization in Healthcare Environments", IEEE International Conference on Development and Application Systems, May 15-17, 2014, 7pgs.
Yan et al., "SAMMPLE: Detecting Semantic Indoor Activities in Practical Settings using Locomotive Signatures", IEEE International Symposium on Wearable Computers, Jun. 18-22, 2012, 5 pgs.
Yang et al., "Locating in Fingerprint Space: Wireless Indoor Localization with Little Human Intervention", Proceedings of the International Conference on Mobile Computing and Networking, Aug. 22-26, 2012, pp. 269-280.
Yang et al., "Projected Supply of and Demand for Oncologists and Radiation Oncologists Through 2025: An Aging, Better-Insured Population Will Result in Shortage", Journal of Oncology Practice, vol. 10, No. 1, Jan. 2014, pp. 39-45.
Yang et al., "Using acceleration measurements for activity recognition: An effective learning algorithm for constructing neural classifiers", Pattern Recognition Letters, vol. 29, No. 16, Dec. 2008, pp. 2213-2220.
Youssef et al., "PinPoint: An Asynchronous Time-Based Location Determination System", Proceedings of the International Conference on Mobile Systems, Applications, and Services, Jun. 19-22, 2006, pp. 165-176.
Yu et al., "Development of Short Forms from the PROMIS Sleep Disturbance and Sleep-Related Impairment Item Banks", Behavioral Sleep Medicine, vol. 10, No. 1, Dec. 28, 2011, pp. 6-24.
Zaruba et al., "Indoor location tracking using RSSI readings from a single Wi-Fi access point", Wireless Networks, vol. 13, No. 2, Apr. 2007, Published Online: Jun. 8, 2006, pp. 221-235.
Zhang et al., "A Feature Selection-Based Framework for Human Activity Recognition Using Wearable Multimodal Sensors", BodyNets International Conference on Body Area Networks, Nov. 7-8, 2011, pp. 92-98.
Zhang et al., "I Am the Antenna: Accurate Outdoor AP Location using Smartphones", Proceedings of the International Conference on Mobile Computing and Networking, Sep. 19-23, 2011, pp. 109-120.
International Preliminary Report on Patentability for International Application PCT/US2016/037398, dated Dec. 19, 2017, dated Dec. 28, 2017, 9 Pgs.
International Search Report and Written Opinion for International Application No. PCT/US2016/037398, Search completed Aug. 24, 2016 dated Sep. 19, 2016, 11 Pgs.
Leaf Healthcare: Resources, Feb. 28, 2016, Retrieved from: http://www.leafhealthcare.com/resources.cfm.
"World Population Prospects: The 2008 Revision", United Nations, Department of Economic and Social Affairs, 2009, 107pgs.
Aaldriks et al., "Predictive value of geriatric assessment for patients older than 70 years, treated with chemotherapy", Critical Reviews in Oncology/Hematology, vol. 79, No. 2, Aug. 2011, Electronic Publication: Aug. 14, 2010, pp. 205-212.
Alshurafa et al., "Anti-Cheating: Detecting Self-Inflicted and Impersonator Cheaters for Remote Health Monitoring Systems with Wearable Sensors", IEEE International Conference on Wearable and Implantable Body Sensor Networks, Jun. 16-19, 2014, 7 pgs.
Alshurafa et al., "Improving Compliance in Remote Healthcare Systems Through Smartphone Battery Optimization", IEEE Journal of Biomedical and Health Informatics, vol. 19, No. 1, Jan. 2015, Electronic Publication: Jun. 9, 2014, pp. 57-63.
Alshurafa et al., "Robust human intensity-varying activity recognition using Stochastic Approximation in wearable sensors", IEEE International Conference on Body Sensor Networks, May 6-9, 2013.
Anderson et al., "Chronic Care: Making the Case for Ongoing Care", Robert Wood Johnson Foundation, Jan. 1, 2010, 43pgs.
Aurenhammer, "Voronoi Diagrams—A Survey of a Fundamental Geometric Data Structure", ACM Computing Surveys, vol. 23, No. 3, Sep. 1991, pp. 345-405.
Bahl et al., "RADAR: An In-Building RF-based User Location and Tracking System", Infocom 2000, Nineteenth Annual Joint Conference of the IEEE Computer and Communications Societies, vol. 2, Mar. 2000, pp. 775-784.
Bao et al., "Activity Recognition from User-Annotated Acceleration Data", Pervasive Computing, 2004, pp. 1-17.
Baraniuk, "Compressive Sensing", IEEE Signal Processing Magazine, vol. 24, No. 4, Jul. 2007, pp. 118-120, 124.
Bellos et al., "Clinical validation of the CHRONIOUS wearable system in patients with chronic disease", IEEE International Conference of Engineering in Medicine and Biology, Jul. 3-7, 2013, pp. 7084-7087.
Bellos et al., "Identification of COPD Patients' Health Status Using an Intelligent System in the CHRONIOUS Wearable Platform", IEEE Journal of Biomedical and Health Informatics, vol. 18, No. 3, May 2014, Date of Publication: Nov. 27, 2013, pp. 731-738.
Bieber et al., "Sensor Requirements for Activity Recognition on Smart Watches", PETRA International Conference, May 29-31, 2013, 6 pgs.
Bodenheimer et al., "Improving Primary Care for Patients with Chronic Illness: The Chronic Care Model, Part 2", JAMA, vol. 288, No. 15, Oct. 16, 2002, pp. 1909-1914.
Broderick et al., "Patients over 65 years are assigned lower ECOG PS scores than younger patients, although objectively measured physical activity is no different", Journal of Geriatric Oncology, vol. 5, No. 1, Jan. 2014, Electronic Publication: Sep. 5, 2013, pp. 49-56.
Brooke et al., "A Systematic Literature Review with Meta-Analyses of Within- and Between-Day Differences in Objectively Measured Physical Activity in School-Aged Children", Sports Medicine, vol. 44, No. 10, Oct. 2014, pp. 1427-1438.

(56) References Cited

OTHER PUBLICATIONS

Bulusu et al., "Self-Configuring Localization Systems: Design and Experimental Evaluation", ACM Transactions on Embedded Computing Systems, vol. 3, No. 1, Feb. 2004, pp. 24-60.
Cebul et al., "Electronic Health Records and Quality of Diabetes Care", The New England Journal of Medicine, vol. 365, No. 9, Sep. 1, 2011, pp. 825-833.
Cevher et al., "Distributed target localization via spatial sparsity", 16th European Signal Processing Conference, Aug. 25-29, 2008, 5 pgs.
Chaudhry et al., "Telemonitoring for Patients with Chronic Heart Failure: A Systematic Review", Journal of Cardiac Failure, vol. 13, No. 1, Feb. 2007, pp. 56-62.
Chaudhry et al., "Telemonitoring in Patients with Heart Failure", The New England Journal of Medicine, vol. 363, No. 24, Dec. 9, 2010, Electronic Publication: Nov. 16, 2010, pp. 2301-2309.
Chen et al., "FM-based Indoor Localization", Proceedings of the International Conference on Mobile Systems, Applications, and Services, Jun. 25-29, 2012, pp. 169-182.
Chen et al., "Signal Strength Based Indoor Geolocation", IEEE International Conference on Communications, Apr. 28-May 2, 2002, pp. 436-439.
Comsa et al., "Source Localization Using Time Difference of Arrival Within a Sparse Representation Framework", IEEE International Conference on Acoustics, Speech, and Signal Processing, May 22-27, 2011, pp. 2872-2875.
Degen et al., "SPEEDY: A Fall Detector in a Wrist Watch", IEEE International Symposium on Wearable Computers, Oct. 21-23, 2003, 4 pgs.
Della Rosa et al., "Human-Induced Effects on RSS Ranging Measurements for Cooperative Positioning", International Journal of Navigation and Observation, 2012, pp. 1-13.
Dent et al., "Frailty and functional decline indices predict poor outcomes in hospitalised older people", Age Ageing, vol. 43, No. 4, Jul. 2014, Electronic Publication: Nov. 19, 2013, pp. 477-484.
Duarte et al., "Structured Compressed Sensing: From Theory to Applications", IEEE Transactions on Signal Processing, vol. 59, No. 9, Jul. 14, 2011, 60 pgs.
Erikson et al., "Future Supply and Demand for Oncologists: Challenges to Assuring Access to Oncology Services", Journal of Oncology Practice, vol. 3, No. 2, Mar. 2007, pp. 79-86.
Feng et al., "Received-Signal-Strength-Based Indoor Positioning Using Compressive Sensing", IEEE Transactions on Mobile Computing, vol. 11, No. 12, Dec. 2012, Date of Publication: Oct. 13, 2011, 12 pgs.
Ghasemzadeh et al., "Wireless Medical-Embedded Systems: A Review of Signal-Processing Techniques for Classification", IEEE Sensors Journal, vol. 13, No. 2, Feb. 2013, Date of Publication: Oct. 3, 2012, pp. 423-437.
Gu et al., "A Survey of Indoor Positioning Systems for Wireless Personal Networks", IEEE Communications Surveys and Tutorials, vol. 11, No. 1, Mar. 4, 2009, pp. 13-32.
Hall et al., "The WEKA Data Mining Software: An Update", ACM SIGKDD Explorations Newsletter, vol. 11, No. 1, Jun. 2009, pp. 10-18.
Hatami et al., "A Comparative Performance Evaluation of Indoor Geolocation Technologies", Interdisciplinary Information Sciences, vol. 12, No. 2, Jan. 2006, pp. 133-146.
He et al., "65+ in the United States: 2005", U.S. Census Bureau, Dec. 2005, 254 pgs., (presented in two parts).
Aaldriks et al. "Prognostic value of geriatric assessment in older patients with advanced breast cancer receiving chemotherapy", The Breast, vol. 22, No. 5, Oct. 2013, Electronic Publication: Feb. 14, 2013, 8 pgs.
Askew et al. "Development of a crosswalk for pain interference measured by the BPI and PROMIS pain interference short form", Quality of Life Research, vol. 22, No. 10, Dec. 2013, Electronic Publication: Mar. 29, 2013, 8 pgs.
Bang et al. "Toward real time detection of the basic living activity in home using a wearable sensor and smart home sensors", IEEE International Conference on Engineering in Medicine and Biology, Aug. 20-25, 2008, 4 pgs.
Becker et al. "Requirements for implementation of localization into real-world assistive environments", PETRA International Conference, Jul. 16-18, 2008, 8 pgs.
Bieber et al. "Ambient interaction by smart watches", PETRA International Conference, Jun. 6-8, 2012, 6 pgs.
Bocquet et al. "Using enhanced-TDOA measurement for indoor positioning", IEEE Microwave and Wireless Components Letters, vol. 15, No. 10, Oct. 2005, 3 pgs.
Chehade et al. "Detecting stumbles with a single accelerometer", IEEE International Conference of Engineering in Medicine and Biology, Aug. 28-Sep. 1, 2012, 6 pgs.
Cheng et al. "Indoor robot localization based on wireless sensor networks", IEEE Transactions on Consumer Electronics, vol. 57, No. 3, Aug. 2011, 6 pgs.
De Craemer et al. "Validity of the Omron pedometer and the actigraph step count function in preschoolers", Journal of Science and Medicine in Sport, vol. 18, No. 3, May 2015, Electronic Publication: Jun. 12, 2014, 6 pgs.
Fontecha et al. "Elderly frailty detection by using accelerometer-enabled smartphones and clinical information records", Journal of Personal and Ubiquitous Computing, vol. 17, No. 6, Aug. 2013, 11 pgs.
Gundrum et al. "Cancer in the oldest old in the United States: Current statistics and projections", Journal of Geriatric Oncology, vol. 3, No. 4, Oct. 2012, 8 pgs.
Hatami et al. "On RSS and TOA based indoor geolocation—a comparative performance evaluation", IEEE Wireless Communications and Networking Conference, Apr. 3-6, 2006, 6 pgs.
Hurria et al. "Identifying vulnerable older adults with cancer: integrating geriatric assessment into oncology practice", Journal of the American Geriatrics Society, vol. 55, No. 10, Oct. 2007, Electronic Publication: Aug. 14, 2007, 5 pgs.
Kaemarungsi et al. "Efficient design of indoor positioning systems based on location fingerprinting", IEEE International Conference on Wireless Networks, Communications, and Mobile Computing, Jun. 13-16, 2005, 6 pgs.
Kannry et al. "Effect of e-prescribing systems on patient safety", Mount Sinai Journal of Medicine, vol. 78, No. 6, Nov. 8, 2011, 7 pgs.
Palmerini et al. "Dimensionality reduction for the quantitative evaluation of a smartphone-based Timed Up and Go test", IEEE International Conference of Engineering in Medicine and Biology, Aug. 30-Sep. 3, 2011, 4 pgs.
Seliktar et al. "Cognition in breast cancer survivors: hormones versus depression", Psycho-Oncology, vol. 24, No. 4, Apr. 2015, First Published: Jul. 5, 2014, 6 pgs.
Shin et al. "Smart Watch and Monitoring System for Dementia Patients", Grid and Pervasive Computing, 2013, 8 pgs.
Shinno et al. "Detection of multiple human location and direction by integrating different kinds of sensors", PETRA International Conference, Jul. 16-18, 2008, 8 pgs.
Sum et al. "Vital Sign Monitoring for Elderly at Home: Development of a Compound Sensor for Pulse Rate and Motion", Studies in Health Technology And Informatics, vol. 117, 2005, 8 pgs.
Ward et al. "Physical function and quality of life in frail and/or elderly patients with metastatic colorectal cancer treated with capecitabine and bevacizumab: an exploratory analysis", Journal of Geriatric Oncology, vol. 5, No. 4, Oct. 1, 2014, Electronic Publication: Jul. 4, 2014, 8 pgs.
Xiao et al. "Comparison and analysis of indoor wireless positioning techniques", IEEE International Conference on Computer Science and Service System, Jun. 27-29, 2011, 4 pgs.

\* cited by examiner

SUBJECT ASSESSMENT USING LOCALIZATION, ACTIVITY RECOGNITION AND A SMART QUESTIONNAIRE

CROSS-REFERENCE TO RELATED PATENT APPLICATIONS

This application is a National Stage Entry of International Application No. PCT/US2016/037398, filed Jun. 14, 2016, which claims the benefit of and priority to U.S. Provisional Patent Application No. 62/175,840 filed Jun. 15, 2015 to Pourhomayoun et al., titled "Smart Assessment in a Box for Complex Patients," and U.S. Provisional Patent Application No. 62/330,730 filed May 2, 2016 to Naeim et al., titled "Indoor Health Monitoring System," the contents of which are incorporated herein by reference in their entirety.

BACKGROUND

It has become acceptable and sometimes desirable to monitor patients within their normal environment, both from a cost perspective and from a perspective of obtaining actual information regarding the patient in their normal environment as opposed to obtaining remembered information or obtaining non-representative data over a short measurement cycle in a clinician's office.

SUMMARY

In an embodiment, a method for subject assessment in an environment includes receiving subject sensor data from a sensor positioned adjacent to a subject, receiving beacon signals from beacons placed at different positions within the environment, processing the beacon signals to determine a location of the subject within the environment based on relative power levels of the received beacon signals, and processing the subject sensor data to determine an activity of the subject.

In an embodiment, a system includes processing circuitry and a memory connected to the processing circuitry. The memory stores instructions executable by the processing circuitry to receive subject sensor data from a sensor positioned adjacent to a subject, process the subject sensor data to determine an activity of the subject, and based on the determined activity of the subject, provide a question to the subject at a graphical user interface.

In an embodiment, a system kit for an intended environment includes beacons, a wearable sensing device, and a computer program product downloadable to a user device. The computer program product storing instructions executable by a processor to receive beacon signals from the beacons placed at different positions within the environment, process the beacon signals to determine a location of the wearable sensing device within the environment based on relative power levels of the received beacon signals, and based on the determined location of the wearable sensing device, provide a question at a graphical user interface.

DETAILED DESCRIPTION

Figure 1:
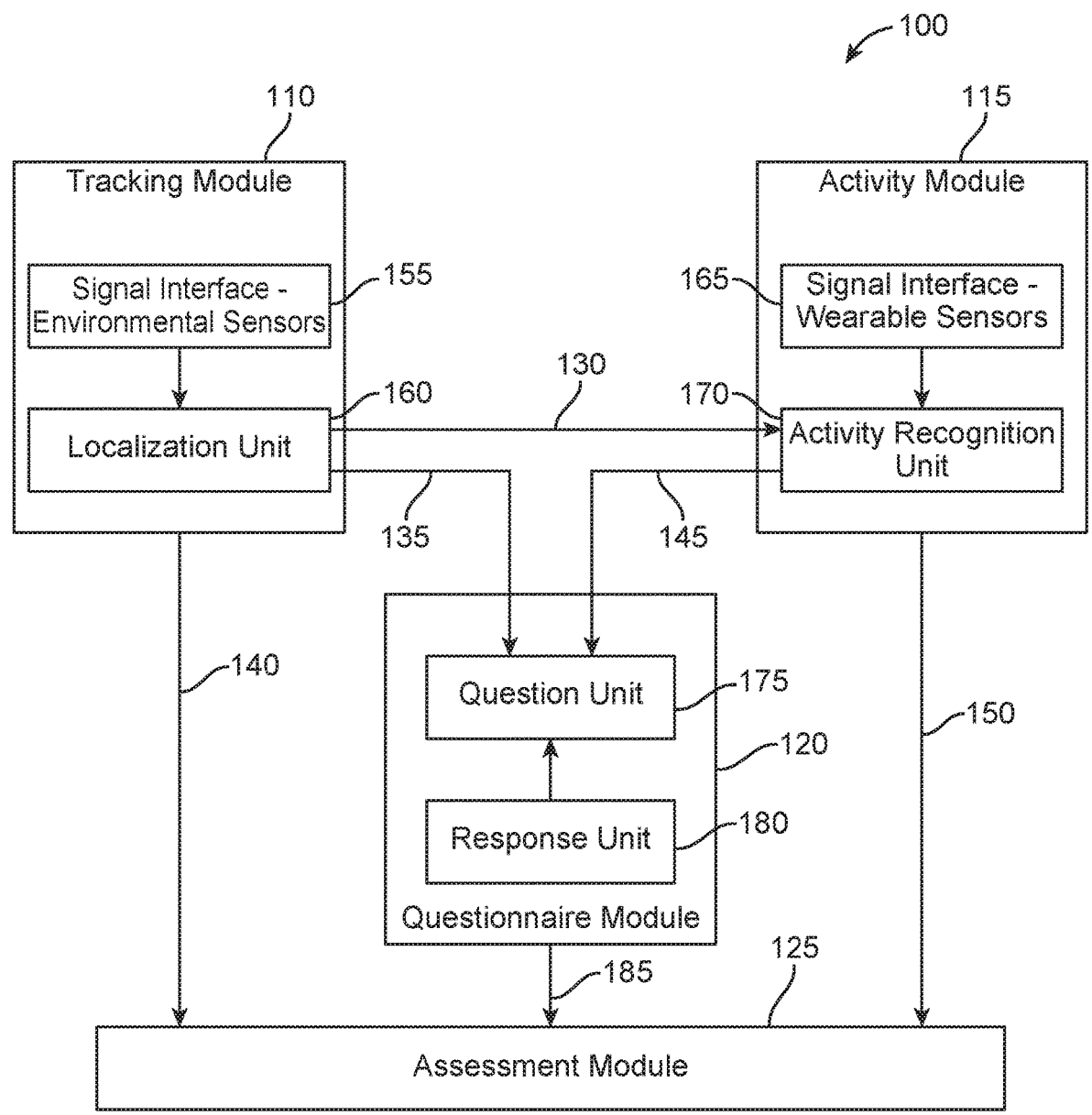
FIG. 1 illustrates an example of a monitoring system according to an embodiment of the present disclosure.

Described herein is a system that provides for monitoring of a subject in their normal environment. This system may be low-cost and easy to install. This system (referred to sometimes as "Smart Assessment in a Box") includes a combination of components such as wearable sensors and devices, in-home or in-facility environmental sensors and devices, and a data processing and analytics engine. The system is installed with little configuration so that knowledge of monitoring systems generally is not a prerequisite to setting up the system described in the present disclosure.

Examples are provided next by way of comparison to existing techniques for oncology patient assessment.

Oncologists often categorize and risk-stratify patients using an Eastern Cooperative Oncology Group (ECOG) Performance Status tool, or other performance status tools, where a performance status value is assigned to a patient, to predict treatment toxicity and outcomes, determine fitness for chemotherapy, and for treatment decision-making purposes. The performance status should be less than a threshold value for the patient to be eligible for many therapeutic clinical trials. An assessment of performance status can be made by a clinician based on patient self-reported activity and fitness, together with clinical information collected verbally and visually during a clinical encounter. The assessment is often imprecise, variable, and highly subjective. Patients with higher levels of performance status (indicating poorer functional status) are often assigned less intensive treatment regimens or are excluded from trials using experimental agents.

By comparison, because performance status is based primarily upon a patient's ambulatory or sedentary time as well as overall activity and location, a monitoring system as disclosed herein can be used for determining and tracking performance status. Determining relevant parameters for such a system can include effectively detecting a discrete number of patient positions or activities and calculating a percentage of overall time the patient spends in each position or activity. The monitoring system can calculate these parameters fairly accurately, to provide a clinician with more objective data relevant to performance status without requiring clinician time and without the clinician's subjective assessment.

Moreover, in some patients, such as older patients, traditional oncology performance status tools are often insufficient to provide a complete assessment of the patient. Geriatric assessment includes aspects of basic activities of daily living and instrumental activities of daily living that are independently prognostic. In addition, geriatric assessment includes evaluation of specific domains such as mood, cognition, nutrition, hearing, and vision. An additional time to perform a geriatric assessment may be 20-60 minutes, and can also suffer from variability based on operator knowledge and the fact that the assessment reflects a single moment in time.

By comparison, a monitoring system as disclosed herein is able to track a patient's status across a range of domains over time, while assessing the patient's status in these domains relative to the patient's own baseline. A more accurate assessment obtained by the monitoring system can lead to a more appropriate assignment of treatment regimen and a more accurate understanding of prognosis, and might assist in avoiding toxicities by informing clinicians regarding patients who are identified as being frail or inactive based upon objective data. Further, an ability to detect decline over time can translate to early warning for timely intervention, which has a potential to reduce treatment cost or decrease morbidity.

More generally, the present disclosure introduces a framework for assessing a subject in an environment. The framework can include wearable and environmental sensors, and advanced analytic techniques and data processing techniques. The system can use a wearable device that can be worn by a subject at all times, interacting with environmental sensors to track the location and mobility of the subject within the subject's normal environment, recognize the subject's activity, and prompt the subject with "smart questions" to gain qualitative feedback, The system of the present disclosure can record and track data over extended periods of time, to provide a determination of the subject across multiple domains in a manner more accurate than an in-clinic assessment.

The framework of the present disclosure can include an automatic assessment of functional and performance status of subjects using machine learning techniques, where a computer automatically performs decision-making about performance status of a subject based on data collected from a monitoring system. To this end, machine learning techniques (particularly a classification or a regression technique) take the monitoring data as input, and generate a predictive model to assess the subject and perform decision-making about the subject's performance status.

In addition, the framework of the present disclosure includes a smart questionnaire module that selects consequential questions for a subject to answer through a graphical user interface. The smart questionnaire automatically determines an appropriate timing (e.g., calculated optimal timing) to deliver each question based on the subject's current and past activity, status, and location. The smart questionnaire can also include a machine learning technique that can learn better timings for delivering questions based on previous answering compliance.

FIG. 1 illustrates an example of a system 100 according to an embodiment of the present disclosure. System 100 includes hardware and software components (the term software encompassing firmware), as will become apparent by the discussions below. Together, the hardware and software components of system 100 provide a capability for monitoring a subject in an environment and assessing various attributes of the subject. The discussion focuses on a single subject for clarity, but it is to be understood that the concepts of the present disclosure encompass monitoring multiple subjects within one or more environments.

System 100 includes a tracking module 110, an activity module 115, a questionnaire module 120 and an assessment module 125. Tracking module 110 provides information to activity module 115 by way of a path 130, provides information to questionnaire module 120 by way of a path 135, and provides information to assessment module 125 by way of a path 140. Activity module 115 provides information to questionnaire module 120 by way of a path 145 and provides information to assessment module 125 by way of a path 150.

Tracking module 110 estimates and tracks an approximate location of a subject in an environment. Tracking module 110 includes a signal interface 155 and a localization unit 160. Signal interface 155 communicates with environmental sensors placed within the environment of the subject. The environment may be indoors or outdoors. Examples of environmental sensors are discussed below. Localization unit 160 receives environment data from signal interface 155 regarding the environmental sensors, and localization unit 160 determines an approximate location of the subject based on the environment data.

Activity module 115 classifies a subject's physical activities. Activity module 115 measures activity level based on collected data from a wearable device associated with the subject. Activity module 115 can include feature extraction, feature selection and dimensionality reduction, and context-aware classification submodules. Activity module 115 can use subject location information received from tracking module 110 as contextual data to achieve more accurate results for the activity classification. Activity module 115 includes a signal interface 165 and an activity recognition unit 170. Signal interface 165 communicates with one or more sensors related to the subject. In FIG. 1, "wearable sensors" are identified and discussed, but it is to be understood that the concepts of the present disclosure encompass also handheld sensors or implanted sensors. Activity recognition unit 170 receives subject data from signal interface 165 regarding the wearable sensors, and also receives subject location information from localization unit 160 in tracking module 110 by way of path 130. The subject location information allows activity recognition unit 170 to determine subject activity with greater accuracy by analyzing subject data (e.g., movement or heart rate) in a context of location of the subject. Examples are provided below.

Questionnaire module 120 selects and delivers consequential questions for a subject to answer through a portable user interface. The delivered questions can validate measures of various components of subject well-being, including but not limited to scales measuring cognition, pain, depression, and sleep quality. Questionnaire module 120 is responsible for selecting the questions and determining the best timing to deliver each question based on a subject's current and past activities from activity module 115 and location from tracking module 110, and also the subject's responses to previous questions. Questionnaire module 120 includes a question unit 175 and a response unit 180. Question unit 175 is "smart" in that it selects appropriate questions and timing of the questions based on context, such as present location information received from localization unit 160 by way of path 135, or such as present or past activity information received from activity recognition unit 170 by way of path 140. Examples are provided below.

Question unit 175 provides determined questions at a determined time to the subject at a graphical user interface of a user device, such as a smart watch, a smart phone, a netbook computer, a notebook computer, or a laptop computer. Response unit 180 receives responses from the subject by way of the graphical user interface, and provides the responses to question unit 175. Question unit 175 uses the responses received from response unit 180 to further determine appropriateness of subsequent questions and timing of the questions. Questionnaire module 120 provides status information to assessment module 125 by way of a path 185.

Assessment module 125 receives information from tracking module 110 by way of path 140, receives information from activity module 115 by way of path 150, and receives information from questionnaire module 120 by way of path 185. Assessment module 125 provides visualization data for displaying the received information, summaries of the received information, or analyses of the received information to an assessor of the subject, such as a caregiver or healthcare provider. Machine learning techniques can be used to build a predictive model that obtains data from tracking module 110, activity module 115, and questionnaire module 120, and then automatically performs decision-making about the subject's functional and performance status.

Paths 130, 135, 140, 145, 150 and 185 represent hardware paths, software paths, or paths that include a combination of hardware and software. For example, localization unit 160 may be incorporated into a device positioned within an environment (e.g., an environment sensor, hub or other computing device), and activity recognition unit 170 may be incorporated into a wearable device on the subject, such that path 130 is a wireless interface including communication hardware components and communication software components for transmitting and receiving information wirelessly. In another example, localization unit 160 and activity recognition unit 170 may be incorporated into a wearable device on the subject, and path 130 is a software interface between software modules, or is a serial interface between integrated circuits.

FIGS. 2A-2D illustrate examples of configurations of components used in system 100, showing a person 210 that is a monitoring subject. It is to be understood that although a person 210 is illustrated and described with respect to FIGS. 2A-2D, other subjects may be monitored instead, such as animals, self-propelled devices, or remotely-controlled devices.

Associated with person 210 is a sensor 220 (labeled 's1'). Although one sensor 220 is illustrated and described, multiple sensors 220 may be used to provide variety, depth or redundancy of information. Sensor 220 may be a vital signal sensor (e.g., heart rate sensor, temperature sensor, oxygen sensor, blood pressure sensor, chemical sensor, etc.) or a motion sensor (e.g., acceleration sensor, position detector, axial movement sensor, yaw, pitch and roll sensor, etc.).

Associated with the environment are sensors 230 and 240 (labeled 's2'). Although two sensors 230/240 are illustrated, it is to be understood that additional sensors s2 may be used. Sensors 230/240 (and any additional sensors) are placed throughout a monitoring environment to provide coverage over a substantial area of the monitoring environment or coverage in one or more key areas of the monitoring environment. Sensors 230/240 may be a similar type of sensor or different types of sensors. For example, both sensor 230 and sensor 240 may be motion detectors, or sensor 230 may be a motion detector while sensor 240 may be an infrared heat detector. In another example, one or both of sensor 230 and sensor 240 is a beacon that emits a beacon signal periodically, or when a presence is detected, or when motion is detected. Beacons are generally defined as sensors that are capable of broadcasting their label or ID or other basic information to the environment. Some beacons are capable of receiving label or ID or other basic information from other beacons.

Figure 2A:
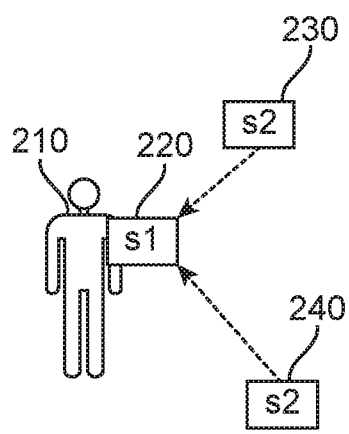
FIG. 2A illustrates an example of a monitoring system configuration according to an embodiment of the present disclosure.

Referring to FIG. 2A, sensor 220, or a device incorporating sensor 220, receives signals or data from sensors 230/240 and processes the signals or data to determine location information of person 210. In one or more embodiments, sensor 220 is incorporated into a computing device, such as in a smart watch or smart phone.

Figure 2B:
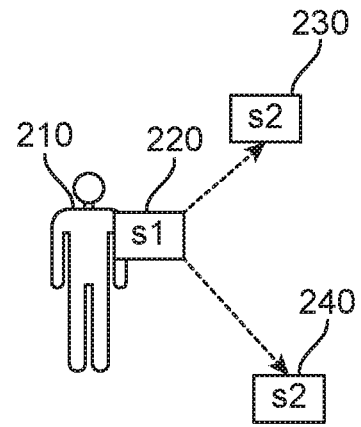
FIG. 2B illustrates an example of a monitoring system configuration according to an embodiment of the present disclosure.

Referring to FIG. 2B, sensor 220, or a device incorporating sensor 220, provides signals or data to sensors 230/240, and one or both of sensors 230/240 determine location information of person 210. In one or more embodiments, a hub device (not shown, which may incorporate one of sensors 230/240 or may be physically apart from both of sensors 230/240) receives information regarding sensor 220 from one or both of sensors 230/240 and determines location information of person 210.

Figure 2C:
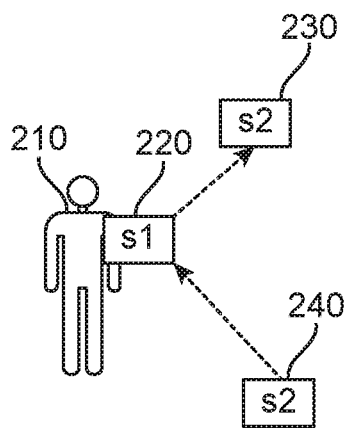
FIG. 2C illustrates an example of a monitoring system configuration according to an embodiment of the present disclosure.

Referring to FIG. 2C, sensor 220, or a device incorporating sensor 220, provides signals or data to sensor 230, and receives signals or data from sensor 240. In this embodiment, sensor 220 may relay information related to the signals or data from sensor 240 to sensor 230 for analysis, or may analyze the signals or data from sensor 240 and provide the analysis to sensor 230. For example, sensor 240 may be an infrared heat detector, which provides data to sensor 220 (or a device incorporating sensor 220) indicating that a heat signature has been identified (presumably person 210), and sensor 220 (or the device incorporating sensor 220) provides the indication of the heat signature to sensor 230, or analyzes the data from sensor 220 to determine proximity of person 210 to sensor 240 and provides the proximity to sensor 230.

Figure 2D:
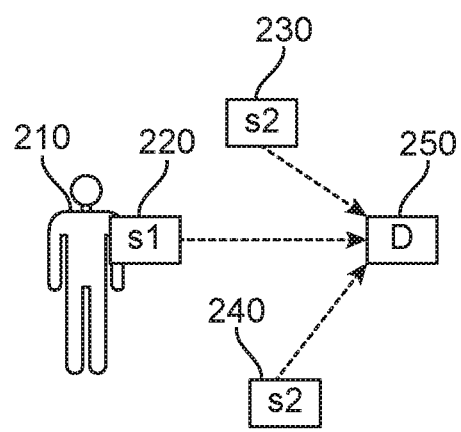
FIG. 2D illustrates an example of a monitoring system configuration according to an embodiment of the present disclosure.

Referring to FIG. 2D, sensor 220, sensor 230, and sensor 240 each provide signals or data to a separate device 250 (labeled 'D') for analysis of the signals or data to determine location information for person 210.

FIGS. 2A-2D are examples of components of system 100 to aid in an understanding of the concepts presented, but are not limiting on the potential configurations of the components of system 100.

Figure 3:
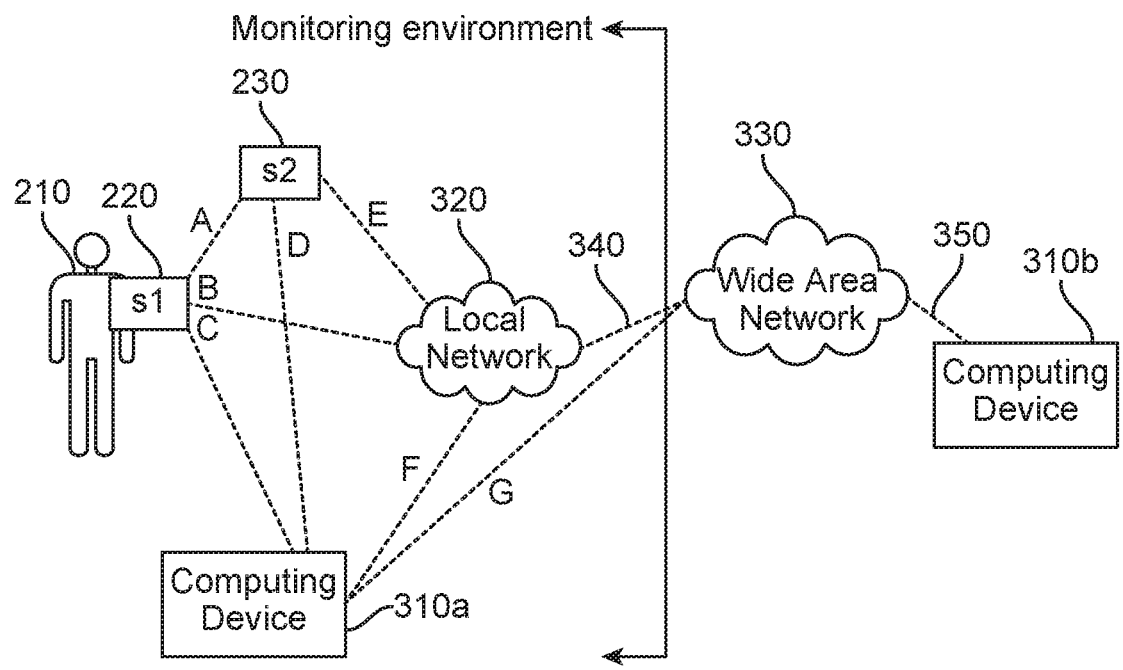
FIG. 3 illustrates an example of a monitoring system according to an embodiment of the present disclosure.

FIG. 3 illustrates a further example of how components of system 100 may be configured. Person 210, sensor 220 and sensor 230 together represent a subject within a monitoring environment. The monitoring environment may be internal or external, such as a room, a house, a physical therapy facility, a detention facility, a residence hall, or an outside area (e.g., exercise area or garden).

Communication paths A, B, C, D, E, F, G represent information exchanges between various components in the monitoring environment. The dotted lines of communication paths A, B, C, D, E, F, G indicate that the communication is optional. For example, sensor 220 may communicate over a communication path A, B or C; over each communication path A, B and C; over communication paths A and B; over communication paths B and C; or over communication paths A and C. The communication paths A, B, C, D, E, F, G that are used depend on the specific physical components in system 100 as well as the configuration of the physical components.

The monitoring environment may include an optional computing device 310a (described generally with respect to computing device 310 in FIG. 4), and an optional local network 320, such as a Wi-Fi protocol network, a BLUETOOTH protocol network, or other local network. Local network 320 may provide communication between components within the monitoring environment, such as between components in a room, or in a house or other facility with multiple rooms.

Figure 4:
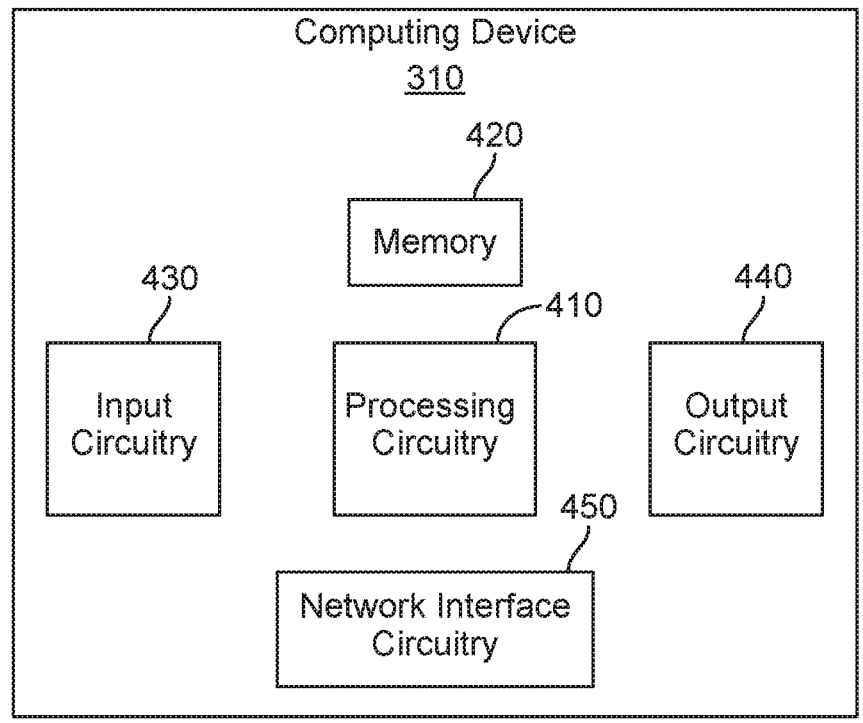
FIG. 4 illustrates an example of a computing device.

In one or more embodiments, information received or analyzed within the monitoring environment is provided external to the monitoring environment through a wide area network 330 to a remote computing device 310b (described generally with respect to computing device 310 in FIG. 4). For example, computing device 310a may provide information (e.g., data or analysis) to computing device 310b through communication path G and wide area network 330 for remote analysis or display. For another example, a device incorporating sensor 220 may provide information (e.g., data or analysis) through communication path B and local network 320 to computing device 310a, which in turn provides the information to computing device 310b.

The following examples refer to FIG. 1 and FIG. 3 together. Tracking module 110 (FIG. 1) may be incorporated in sensor 230 (FIG. 3) or in a hub or other device in communication with sensor 230 (not shown), or in computing device 310a (FIG. 3). Alternatively, signal interface 155 of tracking module 110 (FIG. 1) may be incorporated in sensor 230 (FIG. 1), and localization unit 160 of tracking module 110 (FIG. 1) may be incorporated into the hub or other device in communication with sensor 230 (not shown), or in computing device 310a (FIG. 3). Activity module 115 (FIG. 1) may be incorporated into sensor 220 (FIG. 3) or into a device in which sensor 220 is also incorporated (not shown, e.g., a smart watch or smart phone). Alternatively, signal interface 165 of activity module 115 (FIG. 1) may be incorporated into sensor 220 (FIG. 3), and activity recognition unit 170 of activity module 115 (FIG. 1) may be incorporated in a device (not shown, e.g., a smart watch or smart phone) associated with person 210 or in computing device 310a (FIG. 3). Questionnaire module 120 (FIG. 1) may be incorporated in a device (not shown, e.g., a smart watch or smart phone) associated with person 210, or in computing device 310a (FIG. 3). Assessment module 125 (FIG. 1) may be incorporated in a device (not shown, e.g., a smart watch or smart phone) associated with person 210, in computing device 310a (FIG. 3), or in computing device 310b (FIG. 3). It is to be noted that a smart watch or smart phone is also a computing device (described generally with respect to computing device 310 in FIG. 4). As will be understood, portions of system 100 (FIG. 1) as described with respect to the monitoring environment (FIG. 3) are implemented as software, and thus are implemented as computer-executable instructions on a physical (non-transitory) computer-readable medium.

FIG. 4 illustrates an example of a computing device 310. Computing device 310 includes processing circuitry 410, a memory 420, input circuitry 430, output circuitry 440, and network interface circuitry 450. The components shown are provided by way of illustration and are not limiting. Computing device 310 may have additional or fewer components, or multiple of the same component.

Processing circuitry 410 represents one or more of a processor, microprocessor, microcontroller, application-specific integrated circuit (ASIC), and/or field-programmable gate array (FPGA), along with associated logic.

Memory 420 represents one or both of volatile and non-volatile memory for storing information. Memory 420 is also a computer-readable storage medium, described below.

Portions of system 100 may be implemented as computer-executable instructions in memory 420 of computing device 310, to be executed by processing circuitry 410.

Input circuitry 430 and output circuitry 440 represent electrical components and optional code that together provide an interface from internal components of computing device 310 to external components. Examples include a driver integrated circuit with associated programming, or a sensor interface with filtering circuitry. Input circuitry 430 may provide information regarding external components to processing circuitry 410. Processing circuitry 410 may provide drive or control signals to output circuitry 440 to drive or control external components.

Network interface circuitry 450 represents electrical components and optional code that together provide an interface from the internal components of computing device 310 to external networks, such as network 320 or network 330.

A bus (not shown) may include a dedicated connection between processing circuitry 410 and memory 420. The same bus or a different bus (not shown) may provide a shared connection between processing circuitry 410 and multiple other components of computing device 310.

An embodiment of the present disclosure relates to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the embodiments of the disclosure, or they may be of the kind well known and available to those having skill in the computer software arts. Examples of computer-readable storage media include, but are not limited to: semiconductor devices such as EPROM, EEPROM, ROM, RAM, and flash memory devices, discs such as internal hard drives, removable hard drives, magneto-optical, CD, DVD, and BLU-RAY discs, memory sticks, and other hardware devices that are specially configured to store and execute program code, such as ASICs, FPGAs or programmable logic devices (PLDs).

Examples of computer code include machine code, such as produced by a compiler, and files containing higher-level code that are executed by a computer using an interpreter or a compiler. For example, an embodiment of the disclosure may be implemented using Java, C++, or other object-oriented programming language and development tools. Additional examples of computer code include encrypted code and compressed code. Moreover, an embodiment of the disclosure may be downloaded as a computer program product, which may be transferred from a remote computer (e.g., a server computer) to a requesting computer (e.g., a client computer or a different server computer) via a transmission channel. Another embodiment of the disclosure may be implemented in hardwired circuitry in place of, or in combination with, machine-executable software instructions.

A computer program (also known as a program, software, software application, script, instructions or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a network.

An embodiment of the present disclosure includes a kit with ready-to-install environment sensors (e.g., sensor 230 in FIG. 3), a wearable sensor (e.g., sensor 220 in FIG. 3), and a computer-readable medium with executable instructions for performing portions of the functions of system 100.

Another embodiment of the present disclosure includes a kit with ready-to-install environment sensors (e.g., sensor 230 in FIG. 3), a wearable sensor (e.g., sensor 220 in FIG. 3), and instructions for downloading executable instructions to a computing device (e.g., computing device 310*a* in FIG. 3) from a network site (e.g., a network site in network 330 in FIG. 3).

Another embodiment of the present disclosure includes a kit with ready-to-install environment sensors (e.g., sensor 230 in FIG. 3), a computer-readable medium with executable instructions for performing portions of the functions of system 100, and instructions for downloading a software application to an existing wearable sensor (e.g., sensor 220 in FIG. 3).

In one or more embodiments of a kit, such as an embodiment discussed above, each of the beacons can be preconfigured for placement at a predefined placement position in the environment, such as labeled for placement on a refrigerator, above a bed, in a hallway, and so forth.

Localization

In one or more embodiments, localization of a subject is performed by a one-stage, three-dimensional localization technique based on time-of-arrival signal parameters, received signal strength (RSS), and a spatial sparsity in an x-y-z space, which technique directly estimates location of the subject without calculating time-of-arrival or RSS estimation in a separate, intermediate stage.

In one or more embodiments, localization of a subject is performed using an RSS technique, in which localization is determined according to relative values of RSS between multiple beacons. For example, beacons and a smart watch (or other portable device that can be worn, affixed, or otherwise held adjacent to a human body) are used for monitoring within a subject's normal environment. By placing beacons at multiple locations and comparing RSS indicator (RSSI) values recorded by the smart watch, an approximate location of the subject can be determined.

RSSI is a measurement of a power of a received radio frequency (RF) signal in a wireless network. Localization techniques based on calculating distance by RSSI values can suffer from high variance in RSSI levels, leading to significant errors in localization. For example, an RF signal may be highly susceptible to antenna direction, multi-path effects, lack of line-of-sight, absorption by obstructive objects, diffraction, and propagation loss. Localization also may face challenges related to BLUETOOTH signals (about 2.4 GHz, in the RF range). These impairments may cause a received signal to vary over time, making it difficult to find the nearest beacon at any particular time by calculating distance to each beacon based on RSSI. According to embodiments of the present disclosure, these effects are overcome by determining a highest RSSI value, as opposed to determining distance from each beacon based on RSSI, because actual position with respect to each beacon is not required.

In one or more embodiments, the system utilizes BLUETOOTH Low Energy (BLE) beacons with iBeacon technology. These beacons are installed in fixed locations and broadcast their presence by broadcasting packets of data containing a unique identifier and transmitting signal strength. A software application resident in the smart watch performs passive scans. Upon receiving beacon data packets, the smart watch stores timestamps related to receipt of the packets, the beacon's unique identifier, and RSSI associated with the beacon. Data received from beacons by the smart watch is used to form an understanding about proximity to the surrounding transmitting beacons, by identifying a closest beacon at any given time from the RSSI values. In one or more embodiments, cell networking and noise cancellations techniques are implemented.

For improved accuracy of closest beacon identification, more beacons may be added, for a higher probability that the smart watch is in a line-of-sight of at least one beacon in each location of interest.

For locations in which a beacon is obscured by one or more objects, a transmission power of the beacon's antenna can be adjusted in such a way to counteract the lack of line-of-sight effect. In other words, a lower transmission power is set for antennas of beacons which are unobstructed in an entire room.

There are scenarios in which a location is not of interest, yet signals from beacons near the non-interesting location may create confusion. Neutralizing beacons may be used to neutralize signals in non-interesting locations.

For in-home deployment, it is desired for the approach to be generic, namely the system should achieve optimal results irrespective of home design. One of the main factors to be considered for in-home scenarios is addressing optimal placement of the beacons. An objective is to determine a set of spots that can best represent interesting locations. For instance, an objective is to find a spot within the kitchen in which the beacon transmission will face least interference from other beacons and can yield the best result. Since such problems in computer science are NP-hard, finding the optimal spot through calculation can be challenging. On the other hand, detailed and thorough analysis for each individual home may impede deployment. A combination of techniques such as a Verenoi diagram can be used for finding gaps and to measure maximal breach paths. Techniques for coverage using wireless ad-hoc sensors may implemented as well. A generic set of instructions can be derived for optimal beacon placements and numbers by investigating an effect of beacon density (number of beacons per unit area), beacons per neighborhood (beacons per nominal radio coverage), localization granularity at a certain beacon threshold density and collision among competing beacons. Dynamic beacon transmission may be implemented.

In one or more embodiments, the use of location together with activity detection not only allows for improving activity detection by the probability of the activity occurring in the location, as discussed above, the determined activity may in turn be used to infer location when beacon signal overlap makes it difficult to determine location through comparing RSSI values.

In some embodiments, weighted antenna powers are used. For locations where beacons are obscured with different objects, the transmission power of the beacons' antennas are adjusted in such a way that counteracts a lack of line-of-sight effect. In other words a lower transmission power is set for antennas of beacons which are unobstructed to the entire room, or higher transmission power is set for antennas of beacons in areas of specific interest.

Findings demonstrate that despite low transmitted beacon power (e.g., to conserve battery life), high localization accuracy can be achieved by the embodiments of the present disclosure.

Activity Recognition

As discussed above, a wearable sensor (or handheld device) can be used to collect data from a subject, and the data may be used to determine activity. In one or more embodiments, the wearable sensor can include a triaxial accelerometer and gyroscope.

Figure 5:
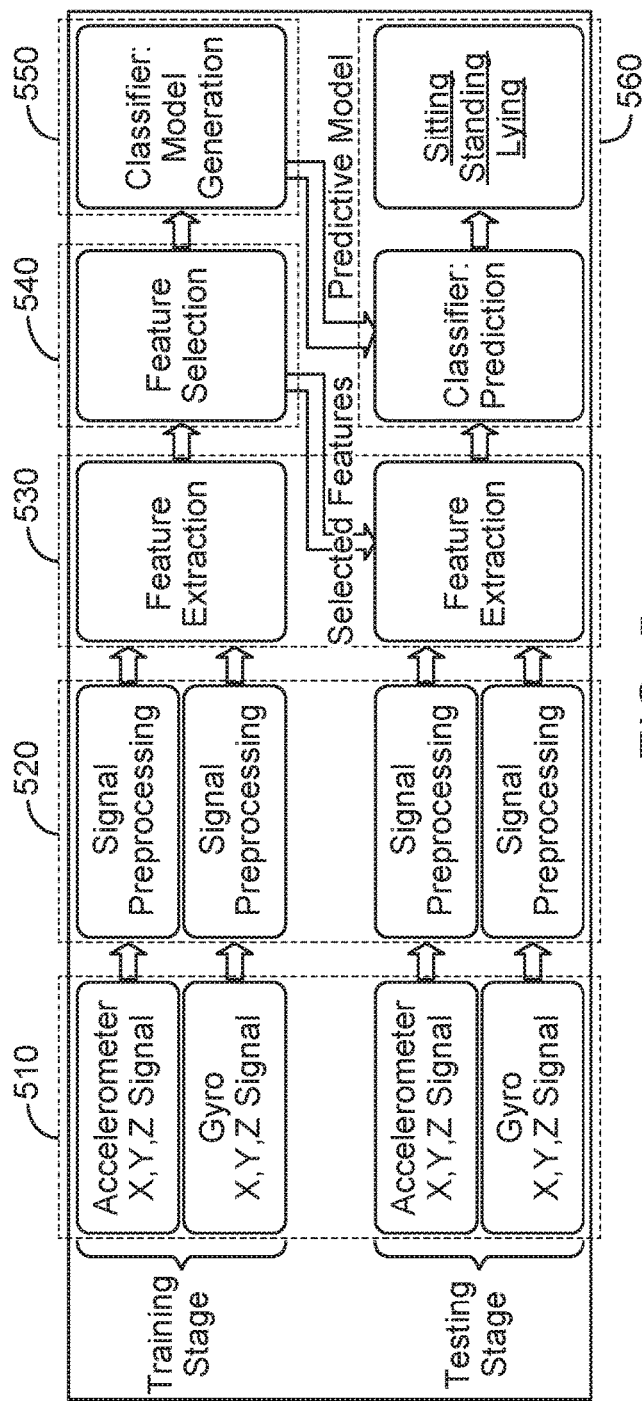
FIG. 5 illustrates an example of a machine learning technique according to an embodiment of the present disclosure.

FIG. 5 illustrates an example of machine learning based approach for activity recognition based on data from a triaxial accelerometer and a gyroscope. The activity recognition includes two main stages: Training Stage and Testing Stage. In Training Stage, the classifier uses a training dataset (with known activity labels) to build a data-driven predictive model. This model is later used in Testing Stage on real data (with unknown labels) to classify and recognize the activity.

In one or more embodiments, the system receives (e.g., FIG. 5, 510) and processes (e.g., FIG. 5, 520) smart watch embedded inertial sensor data for detecting activity and posture: a ±2 g triaxial accelerometer and ±300 degree per second gyroscope sensor. Six signals (three accelerometer signals and three gyroscope signals) are preprocessed and de-noised by applying a low-pass filter. Each of the six signals are divided into 40 second moving window intervals through which features of sampled signals are extracted (e.g., FIG. 5, 530). A total number of 175 statistical features have been extracted from triaxial accelerometer and gyroscope signals in an embodiment. Some of the extracted features include Minimum, Maximum, Sum, Mean, Standard Deviation, Kurtosis, Skewness, Energy, Variance, Median, Root Mean Square (RMS), Average Difference, Interquartile Range, Zero Crossing Rate, Mean Crossing Rate, Eigenvalues of Dominant Directions, CAGH, Average Mean Intensity, Average Rotation Angles, Dominant Frequency, Peak Difference, Peak RMS, Root Sum of Squares, First Peak (Energy), and Second Peak.

Upon extracting a set of features from each window, the system builds a Random Forest classifier with over 100,000 estimators to select the most prominent features for each cluster and reduce redundancy (e.g., FIG. 5, 540). Another classifier, such as another decision tree-based classifier, can be used in place of a Random Forest classifier. In an embodiments, the classifier was built upon 50 subjects over approximately 22 hours of collected data. The cohort of subjects included both subjects using and not using assistive walking devices (canes, walkers) in a rehabilitation center. Positioning can vary dramatically between two people, particularly for elderly and patient populations that can have various trends in their stance, walking or sitting. The system showed good results in inferring the posture over a wide range of subjects: people with usual activity tendencies and people using assistive devices. The demonstrated accuracy of the system allowed the use of a less invasive or disruptive alternative approach.

In an embodiment, both wrapper and filter techniques were used to select features. Wrapper techniques utilize a classifier (or any other learning machine of interest) to evaluate feature subsets in an iterative manner according to predictive power. Filter techniques use a specific metric to score each individual feature (or a subset of features together). Metrics may include correlation coefficient, mutual information, Fisher score, chi-square parameters, entropy, and consistency. A feature subset can be used to train a model that is later evaluated on a testing dataset to assess the relative usefulness of subsets of features.

Once the features are selected, a machine learning based classifier can be applied to classify motions. Machine learning is a type of artificial intelligence that allows computers to learn from data. Machine learning techniques use example data (called Training Dataset) to build a data-driven predictive model (e.g., FIG. 5, 550) that is later used on real data (called Testing Dataset) to make predictions or decisions (e.g., FIG. 5, 560). Classifiers include support vector machine (SVM), Random Forest, Decision Tree, and Naive Bayes classifiers.

As described above, location information is used as contextual data to improve accuracy of the activity classification. For example, the probability of lying in the bedroom is much higher than lying in the kitchen. By knowing the approximate location of the subject (received from the tracking module 110), a better determination about the possible activities that the subject is undertaking can be made. This technique does not ignore unlikely situations because some of them may still happen, such as in emergency cases. The general principle, however, is that the location information can become involved in classifier decision-making as a prior probability distribution to help improve the accuracy of activity detection of the activity module 115.

Assume that c represents the classifier labels and $F_1, \ldots, F_N$ are classifier input features. The classifier probability model can be expressed as a conditional probability $|p(C|F_1, \ldots, F_N)$ (known as Posterior Probability) that can be formulated using Bayes' Theorem as shown in Equation (1).

$$p(C \mid F_1, \ldots, F_N) = \frac{p(C, F_1, \ldots, F_N)}{p(F_1, \ldots, F_N)} \qquad (1)$$

The term $p(F_1, \ldots, F_N)$ (called evidence) is a constant which does not affect the classifier decision-making. The joint probability in the numerator can be reformulated as shown in Equation (2).

$$p(C, F_1, \ldots, F_N) = p(C)p(F_1, \ldots, F_N \mid C) \qquad (2)$$
$$= p(C)p(F_1 \mid C)p(F_2, \ldots, F_N \mid C, F_1)$$
$$= p(C)p(F_1 \mid C)p(F_2 \mid C, F_1)\ldots p(F_N \mid C, F_1, \ldots, F_{N-1})$$

The term $p(F_1, \ldots, F_N|C)$ (called likelihood) is usually determined in the training stage. A Maximum A Posteriori (MAP) decision-making rule can be applied to pick the most probable class label, as shown in Equation (3).

$$\text{classify}(f_1, \ldots, f_N) = \arg\max p(C=c)$$
$$p(f_1, \ldots, f_N \mid C=c) \qquad (3)$$

For an example case (e.g., in a Naive Bayes classifier), the features can be assumed to be conditionally independent. In this case, the equation (13) can be simplified to Equation (4).

$$\text{classify}(f_1, \ldots, f_N) = \arg\max_c \; p\;(C = c) \prod_{i=1}^{N} p(F_i = f_i \mid C = c) \quad (4)$$

A uniform distribution for the Prior Probability p(C) can be used. However, in this approach, the subject's location can provide some information about the probability of each label. Thus, p(C) can be written as in Equation (5), where p(C,L) is the joint probability distribution of location and activity label.

$$p(C = c) = \sum_i (C = c, L = l_i) \quad (5)$$
$$= \sum_i p(L = l_i) p(C = c \mid L = l_i) \mid$$

Thus, when the location is known (received from the tracking module 110), the Prior Probability p(C) is replaced by the conditional probability $p(C|L=l_i)$ and consequently, Equation (4) provides more accurate results on the activity recognition.

An in-lab clinical trial was conducted to validate an ability of the system to accurately identify activities. Data was collected from a group of 20 volunteers in a supervised study. In this example, a wearable smart watch (including an embedded accelerometer and gyroscope) was used to collect the activity data. Each subject was asked to perform a set routine of activities meant to train a technique to classify sitting, standing, and lying. A leave-one-subject-out cross validation (LOSO-CV) was used to determine the model's effectiveness over subject populations to avoid the pollution of results in training and testing on the same subject. In LOSO-CV, each time, one of the subjects was selected as a test subject. The data of other subjects was used as a training dataset to build a data-driven predictive model. This model was used to classify and recognize the activity of the test subject. Results are reported in average F-score, where the F-score is an indication of how well the system can identify the movements and how strong it is at not mis-predicting. According to study results, the wearable system provides strong results, with an F-score of 0.930 at sampling rate of 10 Hz and F-score of 0.932 at sampling rate of 100 Hz. This indicates that the system can, in fact, provide strong classifications of transition movements, and as a result, can accurately determine an activity or position of a subject.

In one or more embodiments, a threshold movement level is established, and activity classification includes distinguishing between sitting, lying or standing still versus sitting, lying or standing while performing an activity based on the threshold movement level.

Smart Questionnaire

To achieve more accurate results in performance, functional, geriatric assessment, or other assessment, a smart questionnaire can deliver questions for a subject to answer at a determined optimal time of a day, which is automatically determined for each subject to maximize the subject's compliance. To conduct investigations of a subject in a systematic and detailed way, the smart questionnaire is designed to provide questions that measure underlying psychological constructs. Such questions can be informed by behavioral patterns, which includes capability, opportunity and motivation. The questions are prompted in a smart way, that is, they change according to a subject's status; for instance, asking about "how rested" the subject feels after a few hours of "lying in bed", or "how tired" after a certain amount of walking. Leveraging power optimization techniques (discussed below), the activity recognition can be performed on the smart watch followed by presenting relevant questions.

The smart questionnaire can be installed on a Smart watch, Smart Phone, Tablet, or any other form of electronic user interface. The questions can validate measures of various components of subject well-being, including but not limited to scales measuring cognition, pain, instrumental support, depression, and sleep quality. The smart questionnaire module is responsible for selecting the questions and also for determining an optimal timing to deliver each question based on the subject's current activity, status, and location. For example, questions may be delivered when the subject is not engaged in a complex activity, which may improve responding compliance. For another example, questions may be delivered at a time that has already been successful in practice for the particular subject.

Thus, in an embodiment, one can utilize a machine learning technique that learns the best delivery time of each question for each subject. In such an approach, the smart questionnaire module can start with an initial schedule provided by a clinician. Then, over time, the module (e.g., the machine learning technique) can learn the best timings to deliver each question based on answering compliance feedback and subject status/location received from activity recognition unit 170 and localization unit 160.

In an embodiment, some questions can be asked in specific predefined situations. For example, a question about pain can be asked during or after a specific activity, or a question about shortness of breath can be asked after a long walk.

An optimization technique combined with machine learning techniques can be employed to determine the best question delivery timings for each individual. In an embodiment, Bayesian Optimization can be used as an effective technique for automatically tuning hyperparameters of machine learning models. Bayesian optimization is a sequential technique for global optimization, which considers an unknown objective function as a random function with prior probability distributions. The prior distribution is then updated to form the posterior distribution, which is utilized to determine the next best timing of interest. In other words, Bayesian optimization is used to extract the posterior estimate of the true function given observations and feedback, and the results are then used to determine the next most promising timing at which to query. Using this technique, one can determine the optimal time for delivering a question for a specific subject based on compliance feedback as well as the subject's current activity, status, and location.

A smart questionnaire can provide clinicians with important information that is used in performance and functional assessment of a patient. It is expected that the answers to such validated questions change with the change in a subject's disease state. For example, if a subject were experiencing a functional decline, one would expect answers to affirmative questions regarding pain, reliance on others, and cognitive decline to increase. As a result, the system also provides questions that the subjects answer during the course of use.

Figure 6:
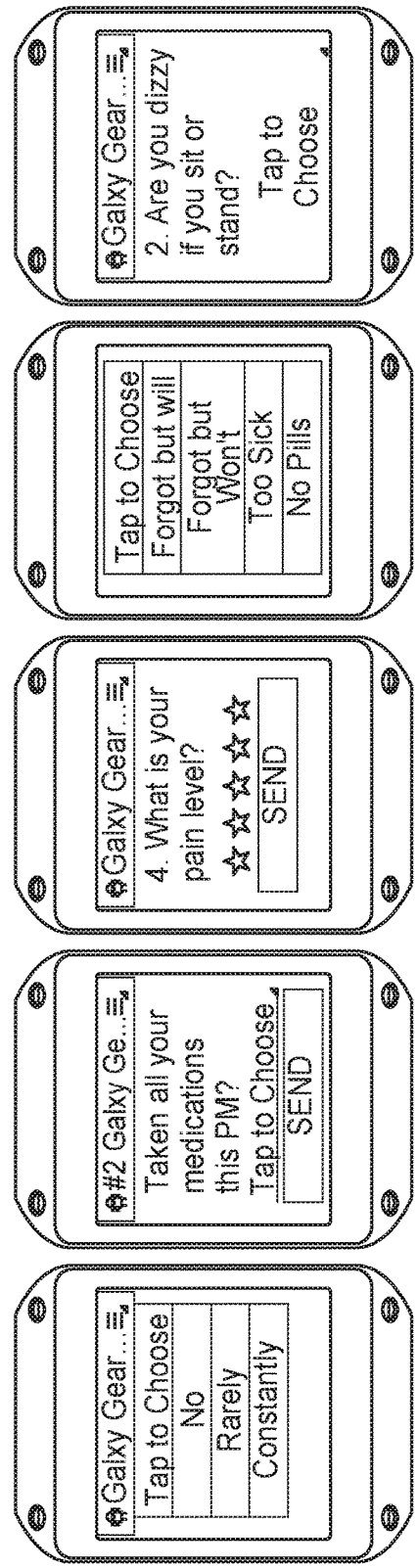
FIG. 6 illustrates examples of questions provided by a smart questionnaire at a graphical user interface according to embodiments of the present disclosure.

FIG. 6 illustrates, by way of example, questions provided at a graphical user interface of a smart watch. By using a user interface (e.g., a touch screen), an application can prompt questions that have either multiple choice answers or ratings of 1 to 5 (or other range). The response information can be provided to a clinician and can aid in assessment, treatment adjustment, or supportive measures.

The following pseudocode is an example of determining an appropriate question and an appropriate time to deliver the question.

```
1: Pos = Position Status
2: Loc = Location Status
3: DataBase = Position(Pos,Loc,Question)
4: procedure SMARTQUESTIONNAIRE(Pos, Loc)
5:     /* Infer if patient is active */
6:     if patientActive then
7:         Question = Query(Pos,Loc)
8:         Trigger(Question)
9:         /* Check if Answered */
10:        if Answered then
11:            Store in DataBase for Medical Investigation
12:        else
13:            Repeat Exponential Back Off Attempt
14:        end if
15:    else
16:        Wait for Activity
17:    end if
18: end procedure
19: /* Query From DataBase */
20: procedure QUERY(Question)
21:     /* Deciding on patients' Activity */
22:     /* Whether Questioning is appropriate (right time) */
23:     /* Deciding on which question is appropriate */
24:     Relations:
25:     Moving out of house: Q1
26:     Inactive in front of TV: Q2
27:     Inactive in Kitchen: Q3
28:     Sitting for a long time: Q4
29:     ...
30:     Return Question
31: end procedure
```

Subject Assessment

Based on data from tracking module 110, activity module 115 and questionnaire module 120, subject assessment may be performed. In an embodiment, the assessment can be done by a clinician. In an embodiment, machine learning techniques can be used to build a predictive model that obtains the data from tracking module 110, activity module 115 and questionnaire module 120, and automatically performs decision-making about a subject's functional and performance status.

In one or more embodiments, assessment module 125 includes a machine learning technique (particularly a classification or a regression technique) that obtains data collected from tracking module 110, activity module 115 and questionnaire module 120 and builds a predictive model to assess a subject and performs decision-making about the subject's performance status.

It has been determined that the techniques of the present disclosure are effective to provide an assessment of functional mobility or rehabilitation that is highly correlated to existing tools (e.g., Berg Balance Scale, 2-minute walk test, 10-meter walk test, mCTSIB, Dynamic Gait Index, Tenneti Falls Efficacy Scale, Stroke Rehabilitation Assessment, Timed Get Up and Go, Canadian Neurological Scale, Fugal-Meyer Assessment, Barthel Index, High-Level Mobility, Chedoke-McMaster, Rivermead Mobility, Functional Behavior, Executive Index for Spinal Cord Injury, and Five Times Sit-to-Stand), as well as being more efficient in administering than existing tools, a better representation of actual mobility and rehabilitation, or more predictive of clinical outcomes.

It has been determined that the techniques of the present disclosure are effective to provide an assessment of activities of daily living that is highly correlated to existing tools (e.g., Functional Independence Measure, Patient Specific Functional Scale, Four Step Square Test, Box and Block, Frenchay Activities, Canadian Occupational Scale, AHO Quality of Life Brief, Needs Assessment Checklist, and ADLS Geriatric Assessment), as well as being more efficient in administering than existing tools, a better representation of actual activities of daily living, or more predictive of clinical outcomes.

It has been determined that the techniques of the present disclosure are further effective to provide an assessment of quality of life that is highly correlated to existing tools (e.g., Medical Outcomes Study Short Form, Nottingham Health, Stroke Specific Quality of Life, WHO Quality of Life-Bref, Life Satisfaction Questionnaire, Satisfaction with Life Scale, Short Form—12 items, Short Form—36 items, Health Utilities Index-3, Euroqol 5 qd, and SF-6D), as well as being more efficient in administering than existing tools, a better representation of quality of life, or more predictive of clinical outcomes.

It has been determined that the techniques of the present disclosure are further effective to provide an assessment of symptoms that is highly correlated to existing tools (e.g., nausea, vomiting, pain, fatigue, depression, anxiety, diarrhea, constipation, incontinence, shortness of breath, and NCI adverse events), as well as being more efficient in administering than existing tools, a better representation of symptoms, or more predictive of clinical outcomes.

It has been determined that the techniques of the present disclosure are further effective to provide an assessment of social support and network that is highly correlated to existing tools (e.g., MOS Social Support, Duke-UNC Social Support, Social Support Questionnaire, Close Persons Questionnaire, Perceived Social Support Scale, and Norbeck Social Support), as well as being more efficient in administering than existing tools, a better representation of social support and network, or more predictive of clinical outcomes.

It has been determined that the techniques of the present disclosure are further effective to provide an assessment of oncology performance measures that is highly correlated to existing tools (e.g., ECOG-PS and Karnovsky), as well as being more efficient in administering than existing tools, a better representation of oncology performance measures, or more predictive of clinical outcomes.

It has been determined that the techniques of the present disclosure are further effective to provide geriatric assessment that is highly correlated to existing tools (e.g., ADL, IADL, comorbidity, MOS Social Support, MOS Social Activity, falls, hospital anxiety and depression, body mass Index, weight loss, VES-13, e-prognosis, and comorbidity-driven life expectancy), as well as being more efficient in administering than existing tools, a better geriatric assessment, or more predictive of clinical outcomes.

It has been determined that the techniques of the present disclosure are further effective to provide an assessment of disease-specific measures that is highly correlated to existing tools, as well as being more efficient in administering than existing tools, a better assessment of disease-specific measures, or more predictive of clinical outcomes.

Power Optimization

Smart watches can exhibit high rates of battery drain associated with BLUETOOTH scanning. Thus, although BLE sensors use significantly lesser power than legacy versions, when BLE sensors are used (e.g., sensor 230 in FIG. 3), a lack of support for batched scans can dramatically affect battery life. In addition, smart watch embedded positioning sensors contain relatively small memory storage, resulting in frequent central processing unit (CPU) wake-ups during scans. To address these issues, in one or more embodiments, scans are modeled as time windowed functions, and implemented over a scanning duty cycle of variable duty factor and period. The period is determined empirically to reveal a reasonable trade-off between continuity of data and frequency of power-cycling the RF module. Each duty cycle is grouped into power mode profiles, which can be selected dynamically at run-time. This added flexibility provides the system with an adaptive scan mode. The system achieves 8 hours 45 minutes of continuous scans, at a duty cycle of 10% with period 2000 milliseconds (ms). More generally, the scanning duty cycle, which represents a percentage of one period in which there is active scanning, can be in a range of 0% to about 100%, such as no greater than about 90%, no greater than about 70%, no greater than about 50%, or no greater than about 30%. Further, with improvements in original equipment manufacturer (OEM) compliance with hardware support for batched-scanning (standard BLUETOOTH v4.2), power consumption is expected to significantly drop.

Activity-Triggered Exponential Back-Off

Considering a number of effective samples per second received by beacons in different interval windows, and modeling the probability of a subject's movements or activities as a Poisson distribution accordingly, a minimum two-fold improvement in battery life and minimum of two-thirds reduction in recorded data size were obtained, while simultaneously improving localization results. A sampling period is determined that is "focal", such that increasing sampling will not result in proportionally increasing a number of samples. Keeping the focal sampling period into consideration, by modifying a windowing function and duty cycle and harnessing motion co-processor capabilities, a battery life enhanced significantly. A low-power sensor built in certain smart watches gives the leverage of applying the modified duty cycle and windowing functions whenever the subject is moving, and keeping a processor in sleep mode the rest of the time. As a result the power drain drops by about a factor of ten. The system of some embodiments ensures a minimum of about 14 hours of battery life for a highly active subject, and can last up to about 24 hours based on empirical analysis.

An "exponential back-off" can be used, in which a duty cycle is decreased from 36% to 18%, then 5% and subsequently 2% in case of not observing any surrounding beacons. 2% is the least duty cycle as considering the beacons transmitting frequency, we may not receive any significant data in intervals less than 200 ms. Such numbers may vary according to transmission power of beacons. The following pseudocode represents an example of a technique for performing exponential back-off scanning and corresponding optimization.

```
1: ON_PERIOD_MAX = 3600
2: ON_PERIOD_MIN = 160
3: OFF_PERIOD_MIN = 5400
4: TOTAL_PERIOD = ON_PERIOD_MAX + OFF_PERIOD_MIN
5: EPOCHS_SINCE_LAST_SIGNTED = 0
6: procedure GETPERIODS(CurrentPeriod, EpochsSinceLastSighted)
7:   ON_PERIOD_NEW = max
     ( ON_PERIOD_MIN, ON_PERIOD_MAX *
     exp(-1*EPOCHS_SINCE_LAST_SIGHTED))
8:   EPOCHS_SINCE_LAST_SIGHTED = 0
9:   OFF_PERIOD_NEW = TOTAL_PERIOD -
     ON_PERIOD_NEW
```

-continued

```
10:   Return ON_PERIOD_NEW, OFF_PERIOD_NEW
11: end procedure
12: /* Initial State */
13:   ON_PERIOD = ON_PERIOD_MAX
14:   OFF_PERIOD = OFF_PERIOD_MIN
15: /* Cycle Through States */
16: procedure GETPERIODS
17:   while true do
18:     boolbeaconSighted = beginScan(ON_PERIOD, OFF_PERIOD)
19:     if beaconSighted then
20:       EPOCHS_SINCE_LAST_SIGHTED = 0
21:     else
22:       EPOCHS_SINCE_LAST_SIGHTED += 1
23:     end if
24:     ON_PERIOD, OFF_PERIOD = get_Periode(ON_PERIOD,
        EPOCHS_SINCE_LAST_SIGHTED)
25:   end while
26: end procedure
```

In a further technique of exponential back-off based on a Poisson process where the occurrences of events are independent and considering the exponential back-off, in case of failed attempts for sending data over Wi-Fi, the number of attempts is reduced each time with an exponentially increasing interval.

Experimental Setup

Figure 7:
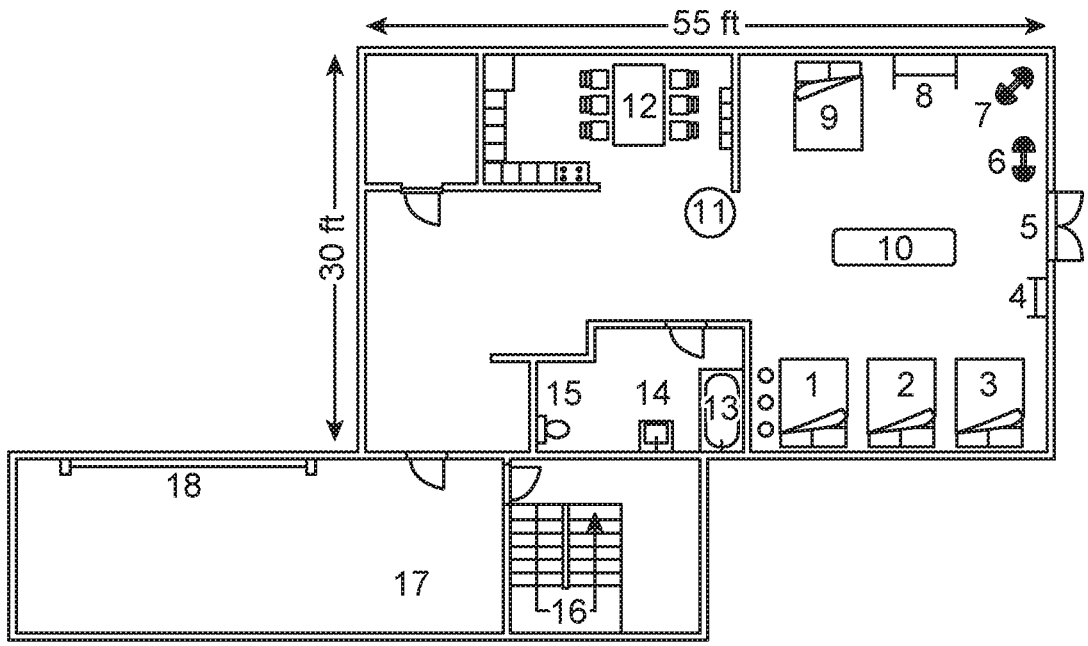
FIG. 7 illustrates a floorplan of a facility in which an embodiment of the present disclosure was tested.
Figure 8:
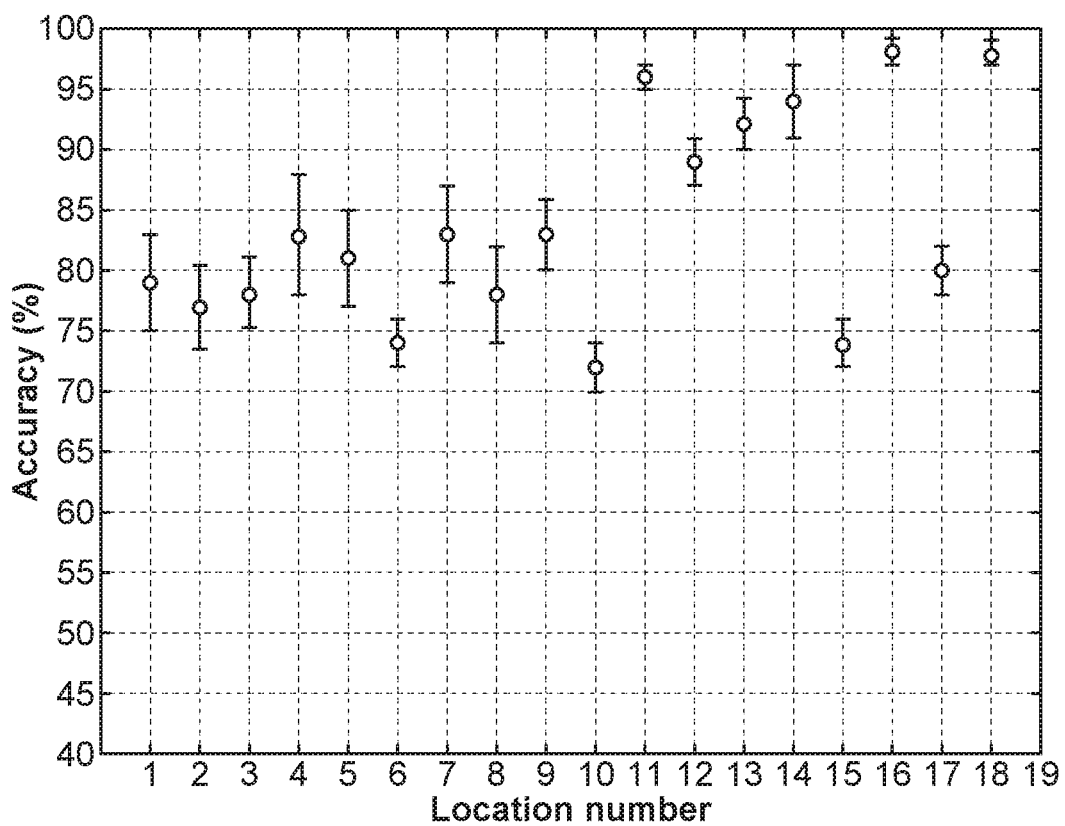
FIG. 8 illustrates location detection accuracy results for a test in the facility of FIG. 7.

The system was developed and enhanced through a series of revisions and modification as the result of implementation in medium and large-sized laboratory environments, and ultimately deployment at a rehabilitation facility in Los Angeles. Detailed experiments have been conducted to assess the performance of the system in each environment. In the rehabilitation center for instance, there were 18 location of interest as shown in a floorplan of the center in FIG. 7. The locations were in close proximity with respect to each other, obstructed by furniture, walls and subjects frequently traversing through them, providing a challenging environment for indoor localization, given the nature of BLE beacons. During experimentation, subjects' locations were logged from 10:00 AM to 4:00 PM over a course of 2 months. The 95%—confidence interval for accuracy for each location is presented in FIG. 8.

Figure 9:
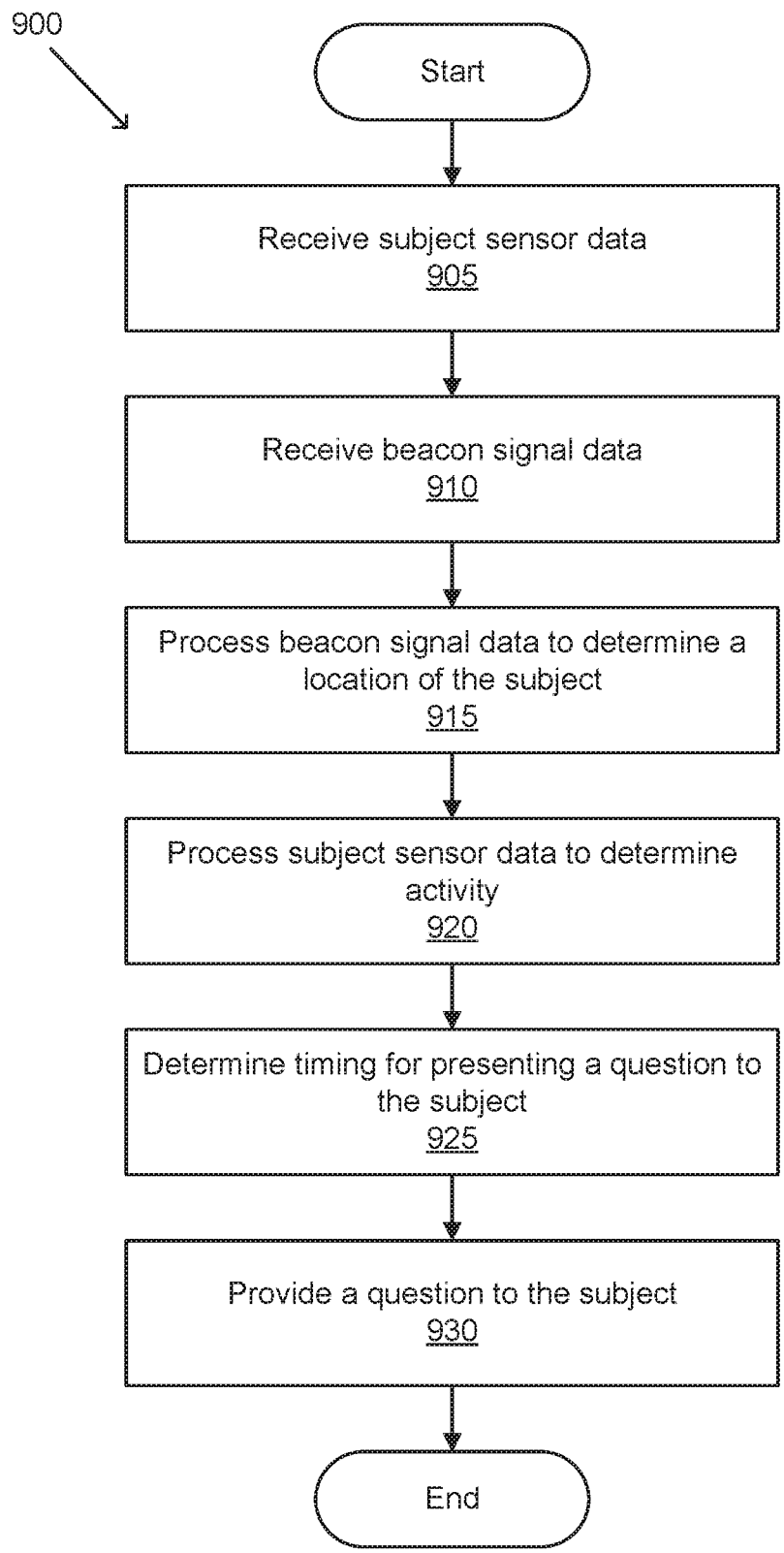
FIG. 9 illustrates an example of a process for subject assessment in an environment.

An example of a process for subject assessment in an environment is illustrated in FIG. 9. Process 900 receives (905) subject sensor data. Process 900 receives (910) beacon signal data. Process 900 process (915) beacon signal data to determine a location of the subject. Process 900 processes (920) subject sensor data to determine an activity of the subject. In numerous embodiments, processing subject sensor data can include using subject location information as contextual data to achieve more accurate results for activity classification. Processes in accordance with various embodiments of the invention can utilize a machine learning based classifier to classify motions. In certain embodiments, processes can establish a threshold movement level to distinguish between sitting, lying or standing still versus sitting, lying or standing while performing an activity. Process 900 determines (925) a timing for presenting a question to the subject. Process 900 provides (930) the question to the subject based on the determined timing.

The system of the present disclosure is ad-hoc deployable, such as in a subject's home. A main constraint for an in-home localization system compared to a rehabilitation environment is a reduced accessibility to the system. As such, the system should be able to operate with minimal configuration and reconfiguration specifications. This constraint means that the system should be self-configurable, namely able to autonomously adapt to environmental changes rather than relying on design/deploy-time pre-configurations or manual setups. This way, the system can ensure a robust, and unattended operation.

As used herein, the singular terms "a," "an," and "the" may include plural referents unless the context clearly dictates otherwise.

As used herein, the terms "connect," "connected," and "connection" refer to an operational coupling or linking. Connected components can be directly or indirectly coupled to one another, for example, through another set of components.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific embodiments thereof, these descriptions and illustrations do not limit the present disclosure. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. A method for subject assessment in an environment, comprising:
   receiving subject sensor data from a sensor positioned adjacent to a subject;
   receiving beacon signals from a plurality of beacons placed at different positions within the environment;
   processing the beacon signals to determine a location of the subject within the environment based on relative power levels of the received beacon signals;
   processing the subject sensor data to determine an activity of the subject;
   determining a timing for providing a question to the subject based on the determined location of the subject and the determined activity of the subject; and
   providing the question to the subject at a graphical user interface based on the determined timing.

2. The method of claim 1, wherein processing the subject sensor data comprises using the determined location of the subject to refine a probability of an activity being the activity of the subject.

3. The method of claim 1, wherein processing the beacon signals includes identifying a beacon signal having a highest power level as indicative of proximity of the subject to a beacon transmitting the beacon signal having the highest power level.

4. The method of claim 1, wherein the subject sensor data comprises motion data from an accelerometer and a gyroscope.

5. The method of claim 1, wherein the environment is a home of the subject.

6. The method of claim 1, wherein the environment is an outside environment.

7. The method of claim 1, further comprising reducing a duty cycle of scanning the beacons based on an exponential back-off power technique.

8. The method of claim 1, further comprising reducing a power level of processing the beacon signals, based on the subject sensor data being indicative of reduced subject activity.

9. The method of claim 1, wherein the subject sensor data comprises inertial sensor data, and processing the subject sensor data includes applying a classifier to the inertial sensor data to determine the activity of the user.

10. The method of claim 9, further comprising establishing a threshold movement level, wherein processing the subject sensor data includes distinguishing between sitting, lying or standing still versus sitting, lying or standing while performing an activity based on the threshold movement level.

11. A system comprising:
    processing circuitry; and
    a memory connected to the processing circuitry, the memory storing instructions executable by the processing circuitry to:
    receive subject sensor data from a sensor positioned adjacent to a subject;
    process the subject sensor data to determine an activity of the subject by analyzing the subject sensor data together with subject location information;
    determining a timing for providing a question to the subject based on the determined location of the subject and the determined activity of the subject; and
    based on the determined activity of the subject, provide a question to the subject at a graphical user interface.

12. The system of claim 11, the memory further storing instructions executable by the processing circuitry to determine a time at which to provide the question based on the determined activity of the subject.

13. The system of claim 11, the memory further storing instructions executable by the processing circuitry to determine a location of the subject based on the subject sensor data and on location information received from at least one beacon.

14. A system kit for an intended environment comprising:
a plurality of beacons;
a wearable sensing device;
a computer program product downloadable to a user device, the computer program product storing instructions executable by a processor to:
  receive beacon signal data from the plurality of beacons placed at different positions within the environment;
  process the beacon signal data to determine a location of the wearable sensing device within the environment based on relative power levels of the received beacon signals; and
  based on the determined location of the wearable sensing device:
    determine a timing for providing a question to the subject; and
    provide the question at a graphical user interface.

15. The system kit of claim 14, wherein the computer program product further stores instructions executable by the processor to receive sensor data from the wearable sensing device when the wearable sensing device is incorporated into the user device.

16. The system kit of claim 15, wherein the computer program product further stores instructions executable by the processor to receive sensor data from the wearable sensing device when the wearable sensing device is incorporated into the user device and the user device is a watch.

17. The system kit of claim 14, further comprising a watch or a handheld device configured to receive the subject sensor data from the wearable sensing device.

18. The system kit of claim 14, wherein each of the beacons is preconfigured for placement at a predefined placement position in the intended environment.

19. The system kit of claim 18, wherein at least one of the beacons is preconfigured to have a higher transmission power than others of the beacons based on its predefined placement position.

* * * * *

UNITED STATES PATENT AND TRADEMARK OFFICE
CERTIFICATE OF CORRECTION

PATENT NO. : 10,937,547 B2
APPLICATION NO. : 15/736744
DATED : March 2, 2021
INVENTOR(S) : Ramin Ramezani et al.

Page 1 of 1

It is certified that error appears in the above-identified patent and that said Letters Patent is hereby corrected as shown below:

In the Specification

Add the following paragraph before Column 1, Line 5:
STATEMENT OF FEDERAL FUNDING
This invention was made with government support under R01 HS024394 awarded by the Agency for Healthcare Research and Quality. The government has certain rights in the invention.

Signed and Sealed this
Sixth Day of June, 2023

Katherine Kelly Vidal
*Director of the United States Patent and Trademark Office*